US006790218B2

(12) United States Patent
Jayaraman

(10) Patent No.: US 6,790,218 B2
(45) Date of Patent: Sep. 14, 2004

(54) OCCLUSIVE COIL MANUFACTURE AND DELIVERY

(76) Inventor: Swaminathan Jayaraman, 459 Lowell Pl., Fremont, CA (US) 94536

( * ) Notice: Subject to any disclaimer, the term of this patent is extended or adjusted under 35 U.S.C. 154(b) by 0 days.

(21) Appl. No.: 09/739,830

(22) Filed: Dec. 20, 2000

(65) Prior Publication Data

US 2002/0010481 A1 Jan. 24, 2002

Related U.S. Application Data

(60) Provisional application No. 60/171,593, filed on Dec. 23, 1999.

(51) Int. Cl.[7] ............................................. A61M 29/00
(52) U.S. Cl. ........................................ 606/191; 606/200
(58) Field of Search ................................... 600/200, 213, 600/151, 157, 158, 194, 191

(56) References Cited

U.S. PATENT DOCUMENTS

| | | |
|---|---|---|
| 4,619,246 A | 10/1986 | Molgaard-Nielsen et al. .. 128/1 R |
| 4,836,204 A | 6/1989 | Landymore et al. .... 128/334 R |
| 4,994,069 A | 2/1991 | Ritchart et al. ............. 606/191 |
| 5,064,435 A | 11/1991 | Porter .......................... 606/12 |
| 5,108,407 A | 4/1992 | Geremia et al. ............ 606/108 |
| 5,108,420 A | 4/1992 | Marks ......................... 606/213 |
| 5,192,301 A | 3/1993 | Kamiya et al. ............. 606/213 |
| 5,382,259 A | 1/1995 | Phelps et al. ............... 606/151 |
| 5,417,708 A | 5/1995 | Hall et al. ................... 606/200 |
| 5,433,727 A | 7/1995 | Sideris ........................ 606/213 |
| 5,443,478 A | 8/1995 | Purdy ......................... 606/200 |
| 5,451,235 A | 9/1995 | Lock et al. .................. 606/213 |
| 5,456,693 A | 10/1995 | Conston et al. ............. 606/192 |
| 5,527,338 A * | 6/1996 | Purdy .......................... 606/200 |
| 5,549,624 A | 8/1996 | Mirigian et al. ............ 606/191 |
| 5,643,317 A | 7/1997 | Pavcnik et al. ............. 606/213 |
| 5,645,558 A | 7/1997 | Horton ........................ 606/191 |
| 5,649,949 A | 7/1997 | Wallace et al. ............. 606/191 |
| 5,658,308 A | 8/1997 | Snyder ........................ 606/191 |
| 5,690,666 A * | 11/1997 | Berenstein et al. .......... 606/191 |
| 5,709,707 A | 1/1998 | Lock et al. .................. 606/213 |
| 5,766,160 A * | 6/1998 | Samson et al. ............. 606/108 |
| 5,879,366 A * | 3/1999 | Shaw et al. ................. 606/213 |
| 5,972,026 A | 10/1999 | Laufer et al. ................. 607/96 |
| 5,976,162 A * | 11/1999 | Doan et al. ................. 606/151 |
| 5,980,554 A * | 11/1999 | Lenker et al. .............. 606/198 |
| 6,010,517 A | 1/2000 | Baccaro ...................... 606/151 |
| 6,024,756 A | 2/2000 | Huebsch et al. ............ 606/213 |
| 6,024,765 A * | 2/2000 | Wallace et al. | |
| 6,033,423 A * | 3/2000 | Ken et al. ................... 606/200 |
| 6,036,720 A | 3/2000 | Abrams et al. ............. 606/213 |

(List continued on next page.)

FOREIGN PATENT DOCUMENTS

WO      WO 9802100 A1 * 1/1998 ........... A61B/17/12

OTHER PUBLICATIONS

R. G. Brabitz et al., "Double–Helix Coil for Occlusion of Large Patent *Ductus arteriosus*: Evaluation in a Chronic Lamb Model", *JACC*, vol. 131, pp. 677–683, 1998.

(List continued on next page.)

*Primary Examiner*—Michael J. Milano
*Assistant Examiner*—Jessica R Baxter
(74) *Attorney, Agent, or Firm*—Fleit Kain Gibbons Gutman Bongini & Bianco; Paul D. Bianco; Martin Fleit

(57) ABSTRACT

The present invention includes a coiled wire formed of a shape memory material for implantation into an anatomical defect. After implantation of one or more of the coiled wires according to the present invention, the defect is occluded and thereby corrected or treated. Prior to implantation, the coiled wire is generally elongated and thereafter it reverts to a predetermined shape that is suitable for occluding the defect. At least one clip having at least two prongs may be provided on the wire for attachment to body tissue. Preferably the wire is made of nickel-titanium. In an alternative embodiment, the coil includes a plurality of layers. At least one of these layers is formed of a shape memory material.

21 Claims, 21 Drawing Sheets

U.S. PATENT DOCUMENTS

| | | | | |
|---|---|---|---|---|
| 6,059,825 | A | 5/2000 | Hobbs et al. | 623/1.18 |
| 6,063,070 | A | 5/2000 | Eder | 606/1 |
| 6,063,100 | A | 5/2000 | Diaz et al. | 606/191 |
| 6,063,104 | A | 5/2000 | Villar et al. | 606/213 |
| 6,074,407 | A | 6/2000 | Levine et al. | 606/194 |
| 6,117,157 | A | 9/2000 | Tekulve | 606/200 |
| 6,126,672 | A | 10/2000 | Berryman et al. | 606/200 |
| 6,159,165 | A | 12/2000 | Ferrera et al. | 600/585 |
| 6,193,708 | B1 * | 2/2001 | Ken et al. | 606/1 |
| 6,241,691 | B1 * | 6/2001 | Ferrera et al. | |
| 6,375,671 | B1 | 4/2002 | Kobayashi et al. | 606/213 |

OTHER PUBLICATIONS

Z. M. Hijazi et al., "Transcatheter closure of large patent *ductus arteriosus* (≧4mm) with multiple Gianturco coils: immediate and mid–term results," *Heart*, vol. 76, pp. 536–540, 1996.

C. J. Murray "Piezo–based system controls spring diameters" *Design News*, May 1996.

E. Rosenthal et al., "Evolving use of embolisation coils for occlusion of the arterial duct," *Heart*, vol. 76, pp. 525–530, 1996.

D. Shim et al., "Follow–Up of Coil Occlusion of Patent *Ductus arteriosus*," *JACC*, vol. 28, pp. 207–211, 1996.

A. Tometzki et al., "Total UK multi–centre experience with a novel arterial occlusion device (duct occlud pfm)," *Heart*, vol. 76, pp. 520–524, 1996.

A. Tometzki, et al., "Transcatheter occlusion of the patent *ductus arteriosus* with Cook detachable coils," *Heart*, vol. 76, pp. 531–535, 1996.

O. Uzun et al., "Transcatheter occulusion of the arterial duct with Cook detachable coils: early experience," *Heart* vol. 76, pp. 269–273, 1996.

J.W. Moore, "Transcatheter Occlusion of Patent *Ductus arteriosus*," *Journal of Interventional Cardiology* 8, pp. 517–530, 1995.

T. Lloyd et al., "Transcatheter Occlusion of of Patent *Ductus arteriosus* With Gianturco Coils," *Circulation* vol. 88, pp. 1412–1420, 1993.

M. Tynan et al., "Transcatheter occlusion of persistent arterial duct," *The Lancet* vol. 340, pp. 1062–1066, 1992.

S. B. Perry et al., "Shunts in Patient With Congenital Heart Disease," *J. Am. Coll. Cardiol.*, vol. 13, pp. 100–108, 1989.

"Tornado Embolization Microcoils," product brochure, undated.

* cited by examiner

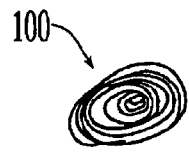
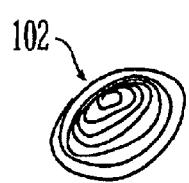
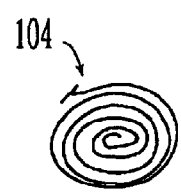
*Fig. 15(a)*  *Fig. 15(b)*  *Fig. 15(c)*
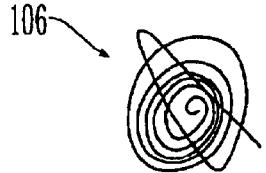
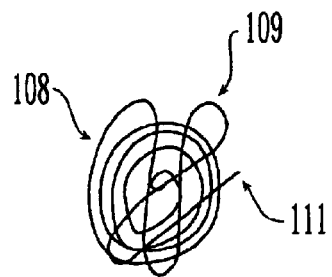
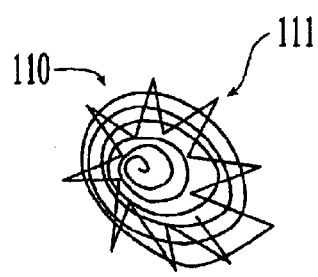
*Fig. 15(d)*  *Fig. 15(e)*  *Fig. 15(f)*
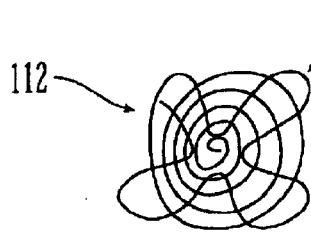
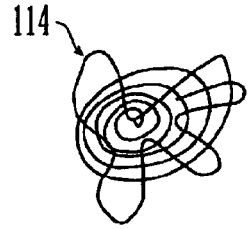
*Fig. 15(g)*  *Fig. 15(h)*
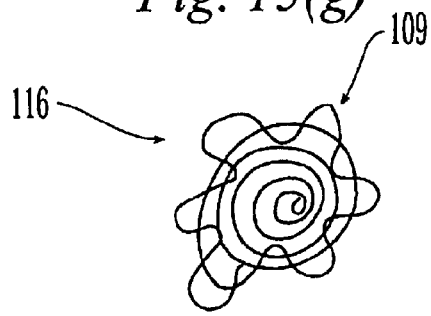
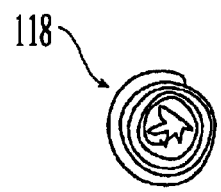
*Fig. 15(i)*  *Fig. 15(j)*

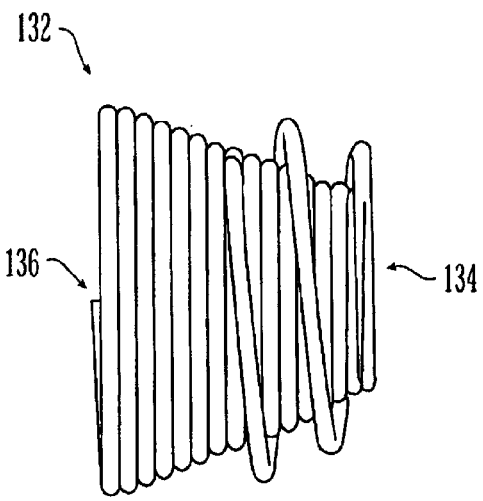
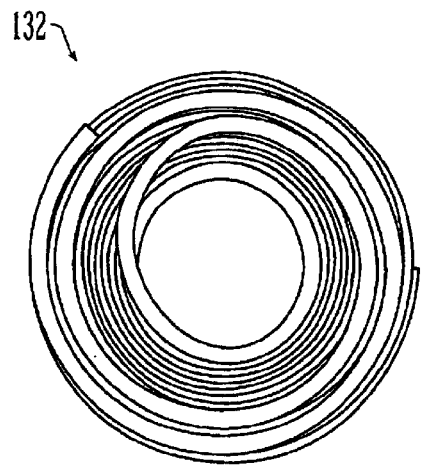
*Fig. 22(a)*  *Fig. 22(b)*
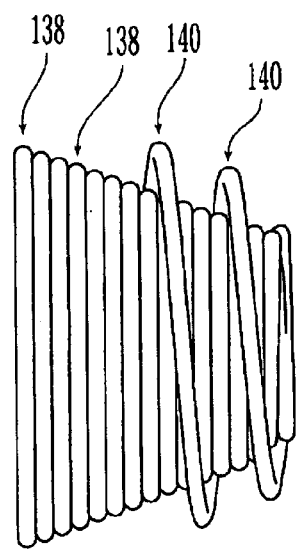
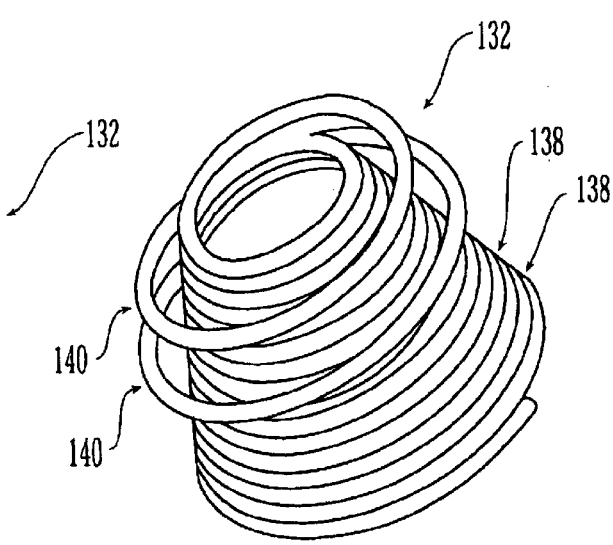
*Fig. 22(c)*  *Fig. 22(d)*

OCCLUSIVE COIL MANUFACTURE AND DELIVERY

CROSS-REFERENCE TO RELATED APPLICATIONS

Priority of Provisional Application Ser. No. 60/171,593 filed Dec. 23, 1999 is claimed under 35 U.S.C. §119(e).

FIELD OF THE INVENTION

The present invention relates to a device for filling an anatomical defect. In particular, the device of the present invention is formed of a member which includes a shape memory alloy.

BACKGROUND OF THE INVENTION

In various body tissues, defects may occur either congenitally or as a result of operative procedures. Such defects may include abnormal openings, for example, in the cardiovascular system including the heart. Procedures have been developed to introduce devices for closing such abnormal openings. Embolization, the therapeutic introduction of a substance into a vessel in order to occlude it, is a treatment used in cases such as patent ductus arteriosus (PDA), major aortopulmonary collateral arteries, pulmonary arteriovenous malformations, venovenous collaterals following venous re-routing operations, occlusion of Blalock-Taussig (BT) shunts, and occlusion of coronary arteriovenous (AV) fistulas.

For example, a PDA is a congenital defect, and thus is present at and exists from the time of birth. In this abnormality, a persistent embryonic vessel connects the pulmonary artery and the aorta, and intervention is usually required to effect closure. A cardiologist may employ a variety of coils for this purpose, the coils being delivered through a catheter and subsequently placed in the opening to permit proper physiological functioning. In some cases, several coils may be used to occlude the opening.

Another abnormality is an atrial septal defect (ASD), which is a defect in the wall of the heart, known as the septum, that separates the right atrium and left atrium. Such as hole in the septum often requires an invasive procedure for closure of the defect. Similarly, intervention is often required in the case of a ventricular septal defect (VSD), a hole in the wall separating the right and left ventricles.

The use of coils in the intracranial region of the brain for embolizing aneurysms or fistulas is also generally accepted.

Each one of the aforementioned exemplary closure applications requires a specially designed coil which may be introduced into the particular anatomical location. For example, the geometry of the lumen in instances of PDA often requires complicated positioning of the coil for proper functioning. Additionally, an initially indeterminate number of coils may be required to close a given defect, as the decision to deliver multiple coils to a particular defect site is governed by the success of any preceding delivery.

A variety of devices and materials have been used to occlude such abnormal channels. For example, U.S. Pat. No. 4,994,069 to Ritchart et al., the contents of which are herein incorporated by reference, discloses vaso-occulusion wire formed of platinum, tungsten, or gold thread. The wire is advanced through a catheter, and upon release from the catheter into a vessel, it assumes a randomly coiled shape. Although the wire of this development is described as having memory, the type of memory property of these materials is not that of a shape memory material having transition temperatures for various material states.

Additionally, U.S. Pat. No. 5,192,301 to Kamiyama et al., discloses a closing plug for closing a defect in a somatic wall. The plug is formed of a polymer such as polynorbornene, styrene-butadiene coploymer, polyurethane, or transpolyisoprene. Although these polymers are described as "shape memory" polymers, they are unlike metallic materials displaying shape memory behavior. Many polymers display a glass-transition temperature ($T_g$) which represents a sharp change that occurs from a hard and glassy state to a rubbery, soft, or flexible thermoplastic state. If deformed by a load at a temperature below its $T_g$, a so-called "shape memory" polymer may retain the deformation until heated above the $T_g$, at which point the deformation and the original shape are recoverable. This characteristic of some polymers is often described as "elastic memory".

A variety of other spring coil configurations have been used, although stainless steel and platinum have emerged as the most common materials. U.S. Pat. No. 5,649,949 to Wallace et al., discloses vosoocclusive coils formed from platinum, gold, rhodium, rhenium, palladium, tungsten, and alloys thereof. Wires formed of composites of these metals and polymers are also disclosed. These materials are inappropriate for the present development because they do not have the shape memory properties of materials such as nitinol. Among the several superior properties of nitinol when compared to stainless steel, the most important include strong physiological compatibility, a substantially lower modulus of elasticity, and a much greater tolerance to strain before the onset of permanent, plastic deformation. In fact, nitinol may have an elasticity an order of magnitude greater than that of stainless steel.

U.S. Pat. No. 5,645,558 to Horton discloses an occlusive device formed of super-elastic alloys, such as nitinol. The device is spherical in shape. U.S. Pat. No. 5,382,259 to Phelps et al. further discloses the use of nitinol shape memory wire to form coils. Fibers are also woven to the coils. These coils do not have the shape of the present development.

Various other coil configurations have been proposed. For example, as disclosed in U.S. Pat. No. 6,117,157 to Tekulve, a helically shaped embolization coil includes bent ends. In addition, U.S. Pat. No. 6,126,672 to Berryman et al. discloses a coil for occluding an intracranial blood vessel. The coil has an anchor in the shape of an "M" or "W" for contacting the blood vessel. The free legs of the anchor are blunted and reinforced to prevent perforation of the vessel wall.

The success and extent of coil usage may be partially gauged through analysis of the PDA coil registry, the largest database covering use of coils to occlude ducts, which surveys more than 500 cases. Among those included in the database, patients ranged in age from 15 days to 71 years, with a median of 4.2 years. The median PDA size was 2 mm, with a range of less than one to about 7 mm. The immediate complete occlusion rate was 75%, and partial occlusion or any degree of shunt occurred in about 25% of the cases. Failure to implant occurred in 5% of the cases. Coil embolization occurred in 9.7% of the cases involving the pulmonary artery, and in 2.4% of the cases involving the systemic artery.

Analysis of data from the coil registry has revealed that an acute occlusion rate and failure was significantly related to coil size. Shorter studies with longer follow up show a cumulative occlusion rate of 98%. While the registry does not address the overall success rate of closure of PDA-associated ducts greater than 4 mm in size because of the statistical limitations of the data set, the immediate results of procedures directed to large ducts are encouraging. Initial complete occlusion occurred in 84.2%, or 16 of 19 cases. In addition, small residual shunts which closed spontaneously or required a second procedure occurred in 10.5%, or 2 of 19 cases, and failure of the procedure necessitating further surgical intervention to effectuate closure occurred in only 5.5%, or 1 of 19 cases. Coil embolization occurred in 16.5%, or 3 of 19 cases, and left pulmonary artery stenosis occurred in 11%, or 2 of 19 cases. It should be noted, however, that left artery stenosis and failure of the procedure were associated with attempts on neonates and infants. Thus, the effectiveness of coils appears to be unquestionably demonstrated.

The device of the present development may be used in a variety of applications, including but not limited to pediatric cardiology procedures directed at occluding either congenital defects or defects arising during the growth process. As previously discussed, such defects include PDA, ASD, VSD, major aortopulmonary collateral arteries, pulmonary arteriovenous malformations, venovenous collaterals following venous re-routing operations, occlusion of Blalock-Taussig (BT) shunts, and occlusion of coronary arteriovenous (AV) fistulas. The device is also useful in treating patent foramen ovale, a persistent opening in the wall of the heart that failed to close after birth.

The device of the present development is also suitable for use in other non-cardiac, vascular procedures. For example, the device may be used in aneurysmal or fistulous conditions. The shape of the device is chosen based on the shape of the defect. In the case of an aneurysm, the device is placed within the aneurysm as a filler, and may be clipped to ends of the aneurysm to anchor it in place. The device occupies the space of the malformation, with the shape of the device chosen to conform with the shape of the defect. Helical, conical, or spiral device shapes are contemplated, among others.

In addition, the device of the present development may be used specifically for neurovascular applications. The device may be delivered to malformations in the brain, such as aneurysms, tumors, or fistulae.

Moreover, the device of the present development may be use in esophageal, tracheal, or other non-vascular applications. In such instances, the device may be used to fill voids, or extra-anatomic space.

SUMMARY OF THE INVENTION

The present invention relates to a device for occluding an anatomical defect in a mammal. The device includes a member formed of a shape memory alloy, the member having a free bottom end and a free top end, a first predetermined unexpanded shape, and a second predetermined expanded shape. The unexpanded shape is substantially linear and the expanded shape is substantially conical, with the expanded shape having a plurality of loops coaxially disposed about a longitudinal axis and progressively decreasing in diameter from one end of the device to the other. At least one of the ends of the member includes a clip having at least two prongs for contacting areas adjacent the anatomical defect.

In one embodiment, the loops form a substantially conical coil having a constant pitch. Alternatively, the loops can form a substantially conical coil having a variable pitch.

The device may be formed of a shape memory nickel-titanium alloy, such as nitinol, and the member may be substantially arcuate in cross-section. At least one of the prongs may additionally include a sharp portion for attaching to an area adjacent the defect. Preferably, the diameter of the plurality of loops is smaller than about 1.5 cm.

The shape memory alloy may display a one-way shape memory effect, or a two-way shape memory effect.

In yet another embodiment, the shape memory alloy displays a superelastic effect at body temperature. Preferably, the shape memory alloy has an austenite finish temperature below body temperature, thereby permitting the device to have superelastic properties at body temperature.

The member may include a plurality of layers. At least one layer may be formed of a passive memory material, and in another embodiment at least two layers may be formed of active memory materials.

In another embodiment, at least one of the layers is a wire formed of a shape memory material, and at least one of the layers is a braid formed of a shape memory material. Preferably, the plurality of layers includes at least two layers braided together or one layer surrounded by a braid.

The device may include at least one crooked section, a substantially conical section, and a substantially cylindrical section disposed between the crooked section and the conical section.

The present invention also relates to a method of occluding an anatomical defect in the vascular tree of a mammal. The method include the steps of: delivering a member formed of a shape memory alloy in a first, substantially straight configuration to an anatomical defect in the body, the member having a temperature below a first transition temperature; and allowing the member to warm above a second transition temperature and form a second, predetermined, coiled configuration having an end with a clip having at least two prongs, wherein the prongs contact areas adjacent the anatomical defect for occlusion of same.

In a preferred embodiment, the second, predetermined, coiled configuration is substantially conical. In another preferred embodiment, the second, predetermined, coiled configuration may include a substantially conical section ending at a free end, at least one crooked section, and a substantially cylindrical section disposed therebetween. Preferably, the second, predetermined, coiled configuration is generally at least one of circular, rectangular, offset coiled, concentric coiled, and combinations thereof.

The present invention further relates to a method of manufacturing a superelastic device for placement inside an anatomical defect, including: providing an inner mandril of a preselected shape for supporting a coil of a wire formed of a shape memory material; winding the wire about the mandril to create a coil conforming to the mandril shape; providing an outer mold to completely surround the coil and mandril and thereby constrain movement of the wire with respect to the mandril; heating the outer mold for a predetermined period of time while the outer mold surrounds the coil and mandril; and allowing the coil to cool.

In addition, the present invention relates to a device for occluding an anatomical defect. The device includes a member formed of a shape memory alloy, the member having a free bottom end and a free top end, a first predetermined unexpanded shape, and a second predetermined expanded shape. The unexpanded shape is sufficiently compact for delivery of the device to the defect. The expanded shape is sufficiently enlarged to occlude the defect by providing a plurality of inner loops and at least one outer loop coaxially disposed about a longitudinal axis, the inner loops progressively decreasing in diameter from a wide end of the device to a narrow end of the device. The at least one outer loop has a diameter greater than the diameter of the inner loops at the narrow end of the device. The device may include at least two prongs for contacting areas adjacent the defect.

The present invention also relates to a method of delivering a device for occluding an anatomical defect. The method includes the steps of: providing a coil having a proximal portion, a transition portion, and a distal portion, and further having an initial length; placing the coil in a movable sheath for delivery to the defect; delivering the movable sheath through the anatomical defect, the anatomical defect having a near side, an inner region, and a far side; withdrawing a portion of the movable sheath from the anatomical defect and allowing the distal portion of the coil to emerge from the sheath; allowing the distal portion of the coil to reach body temperature and expand to a spiral configuration at the far side of the anatomical defect; withdrawing a further portion of the movable sheath from the anatomical defect and allowing the further portion of the coil to emerge from the sheath; and allowing a further portion of the coil to reach body temperature and expand within the anatomical defect.

In a preferred embodiment, the further portion of the coil is the transition portion which expands within the inner region of the anatomical defect. The method may further include the steps of: withdrawing an additional portion of the movable sheath from the anatomical defect and allowing the proximal portion of the coil to emerge from the sheath; and allowing the proximal portion of the coil to reach body temperature and expand to a spiral configuration at the near side of the anatomical defect.

BRIEF DESCRIPTION OF THE DRAWINGS

Preferred features of the present invention are disclosed in the accompanying drawings, wherein similar reference characters denote similar elements throughout the several views, and wherein:

FIG. 22 is another embodiment of a coiled member according to the present invention, shown in (a) side view, (b) top view, (c) side view, and (d) perspective view;

DETAILED DESCRIPTION OF THE PREFERRED EMBODIMENT

In the description which follows, any reference to either direction or orientation is intended primarily and solely for purposes of illustration and is not intended in any way as a limitation to the scope of the present invention. Also, the particular embodiments described herein, although being preferred, are not to be considered as limiting of the present invention.

The most preferred applications of the shape memory alloy members of the present invention are as vasoocclusive devices for filling or blocking anatomical defects, such as openings, in the vascular tree, e.g., holes in veins, arteries or the heart of a mammal. The coil portion of the device is placed or allowed to extend within the opening, where it is contacted by blood. Blood thrombosis upon contact with the coil thus fills in open areas to prevent further blood transport through the defect.

Figure 1:
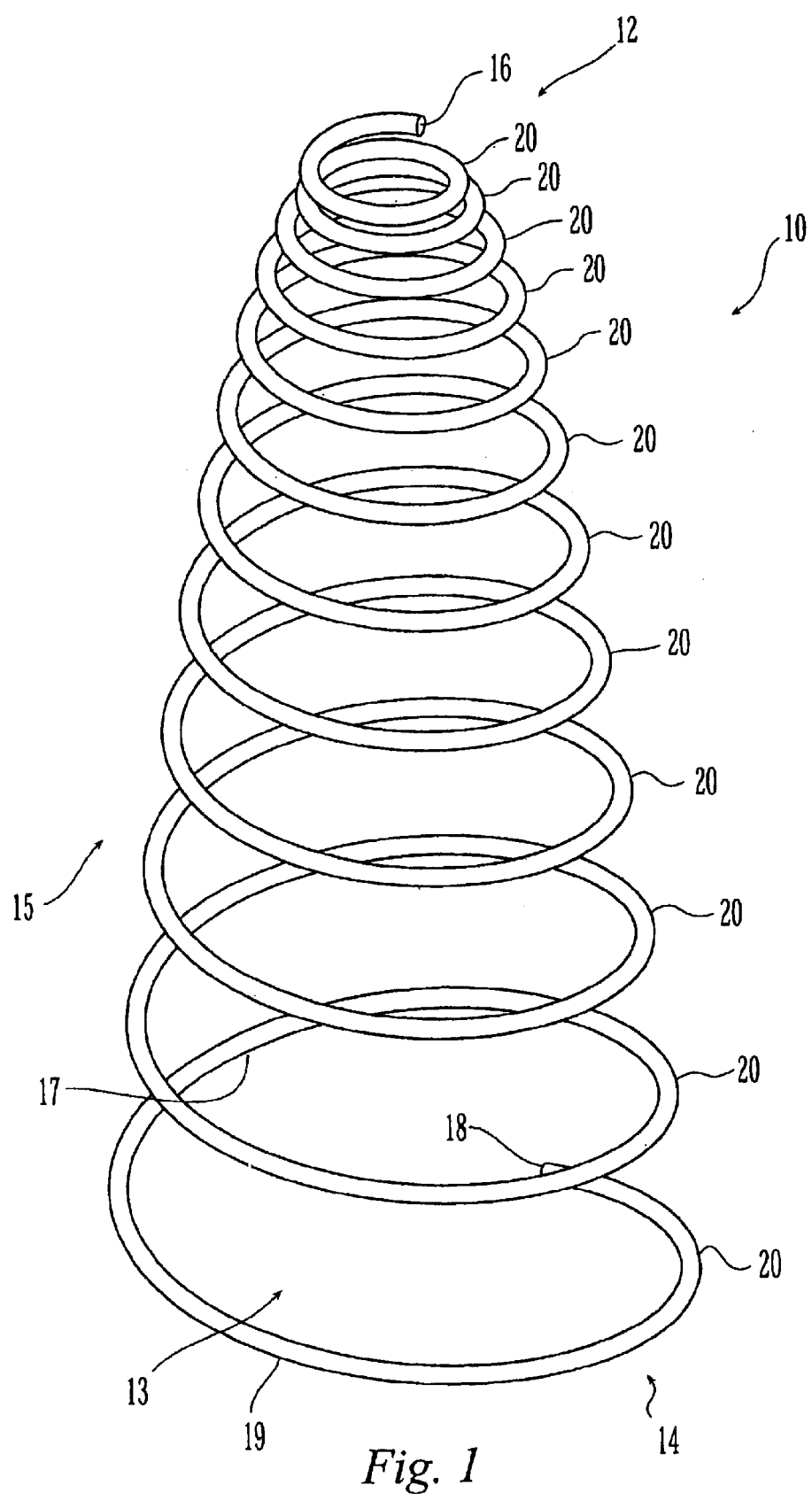
FIG. 1 is a perspective view of one embodiment of a conically coiled member according to the present invention.
Figure 2:
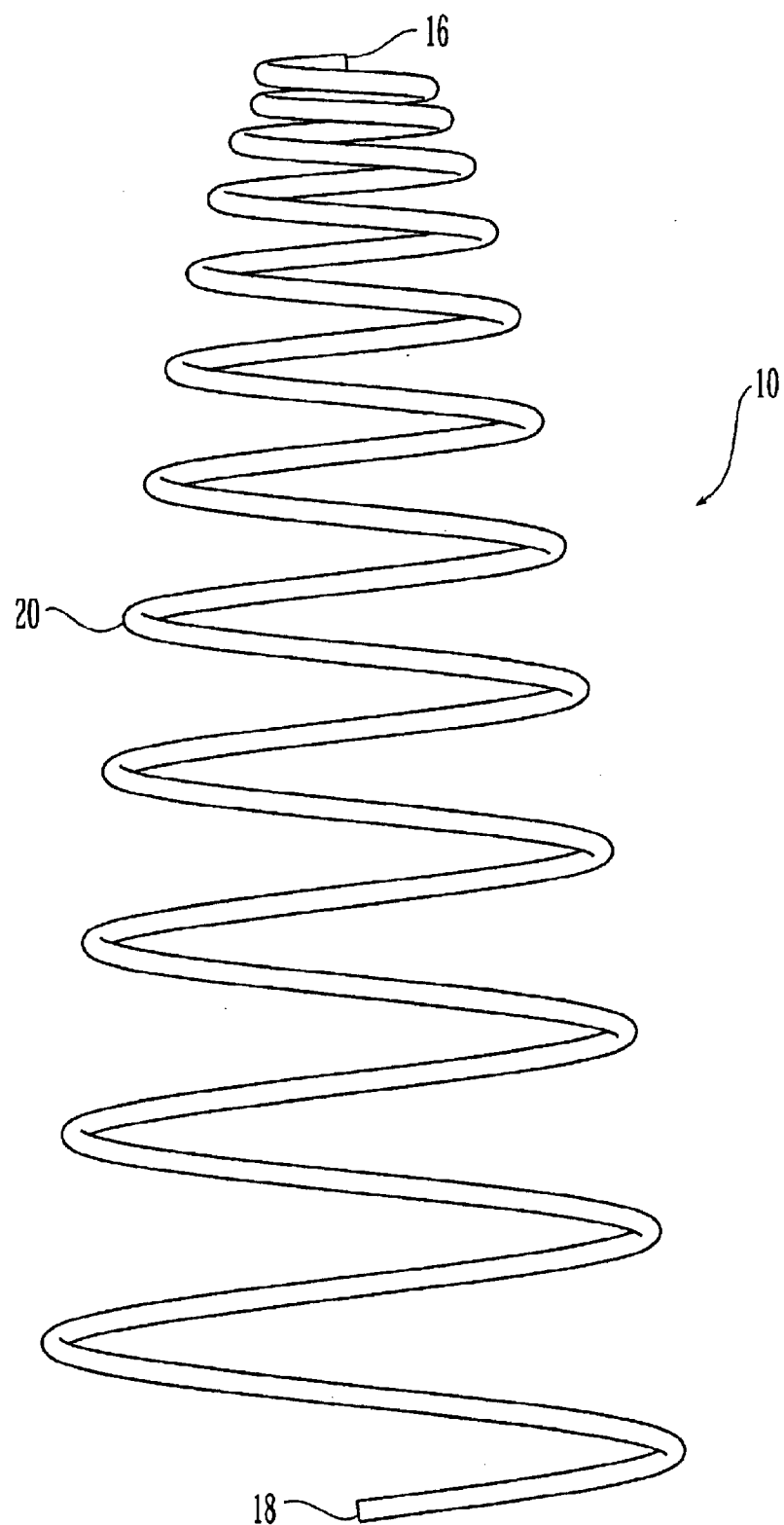
FIG. 2 is a side view of the conically coiled member of FIG. 1.
Figure 3:
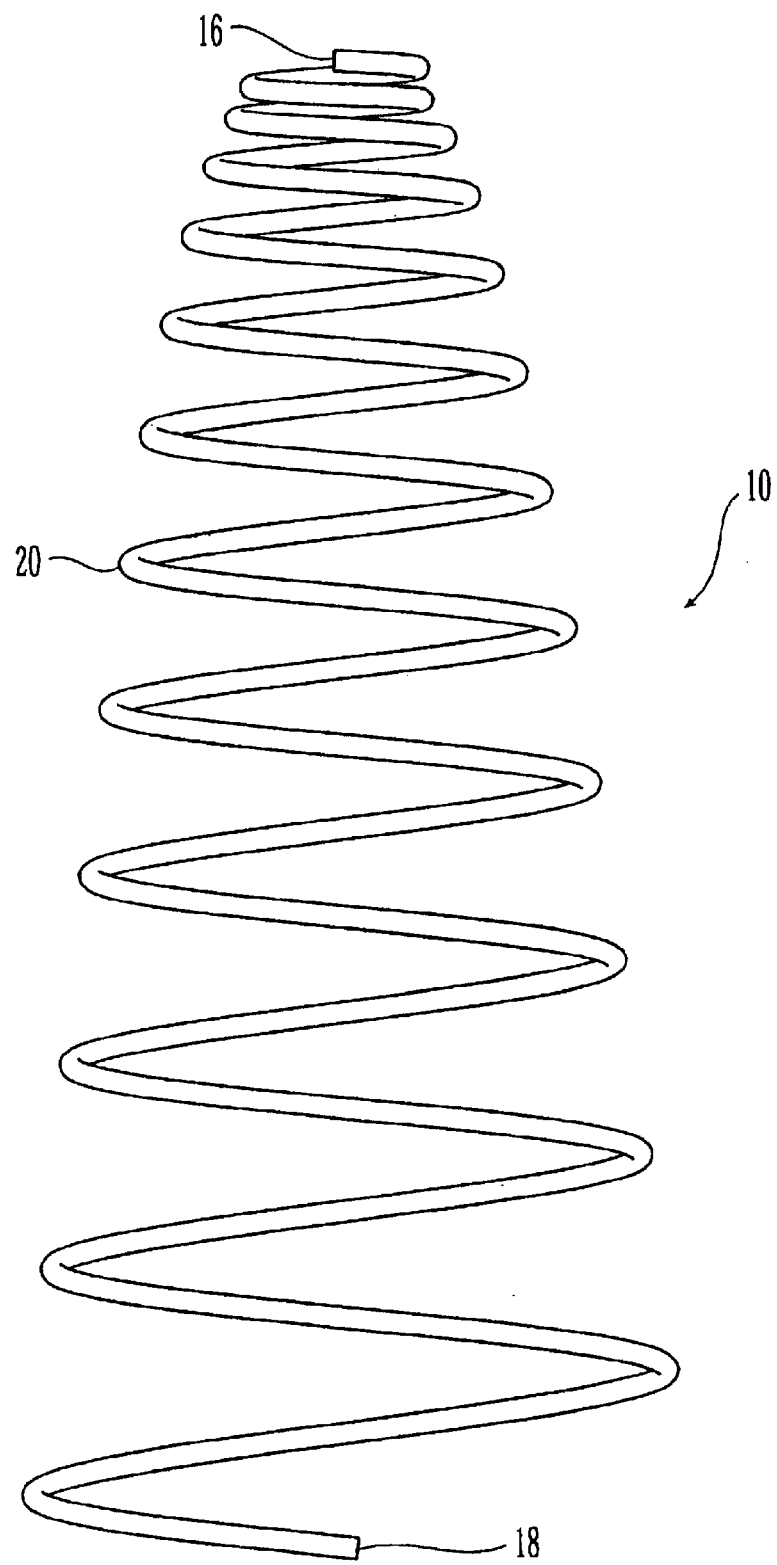
FIG. 3 is another side view of the conically coiled member of FIG. 2 rotated clockwise 180°.
Figure 4:
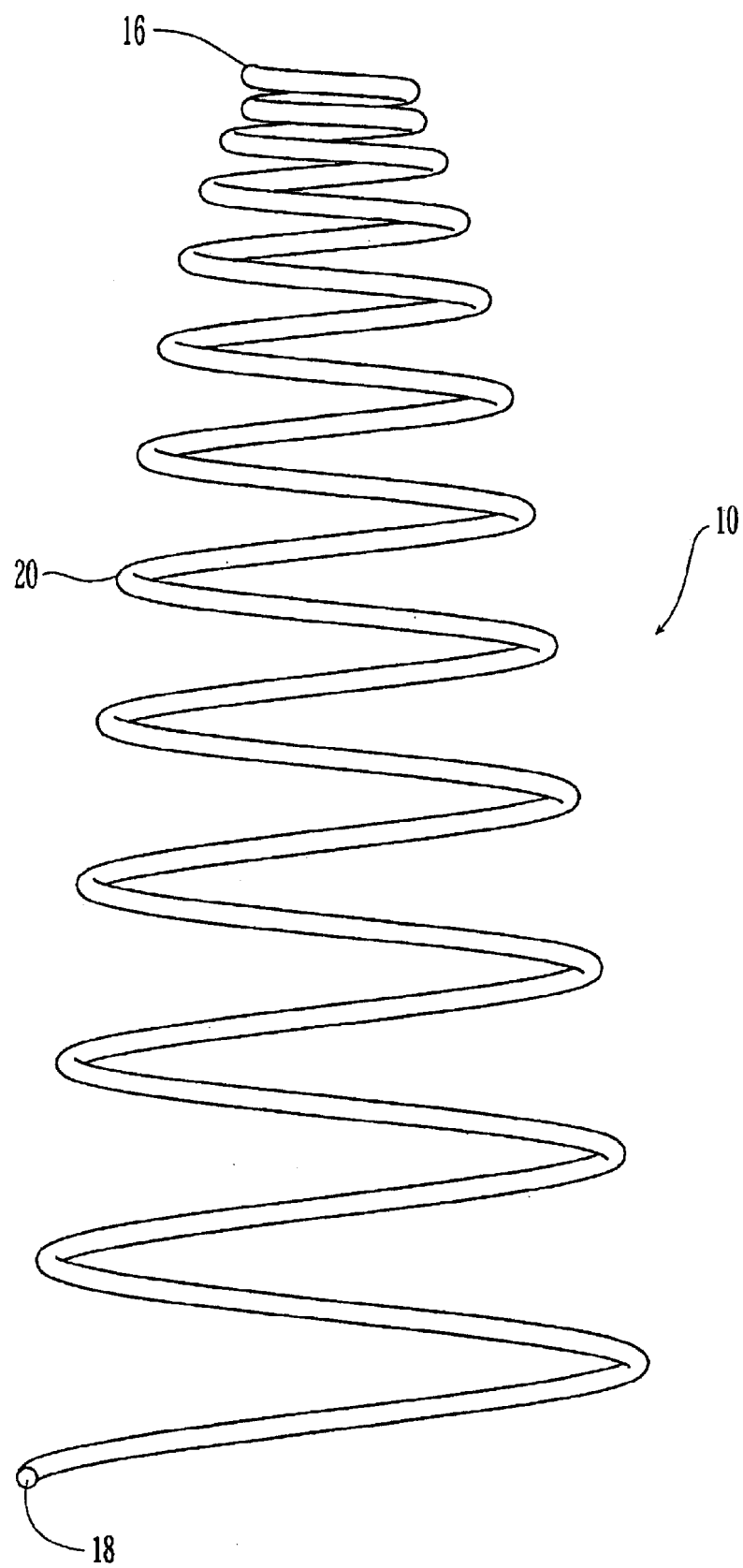
FIG. 4 is another side view of the conically coiled member of FIG. 2 rotated counterclockwise 90°.
Figure 5:
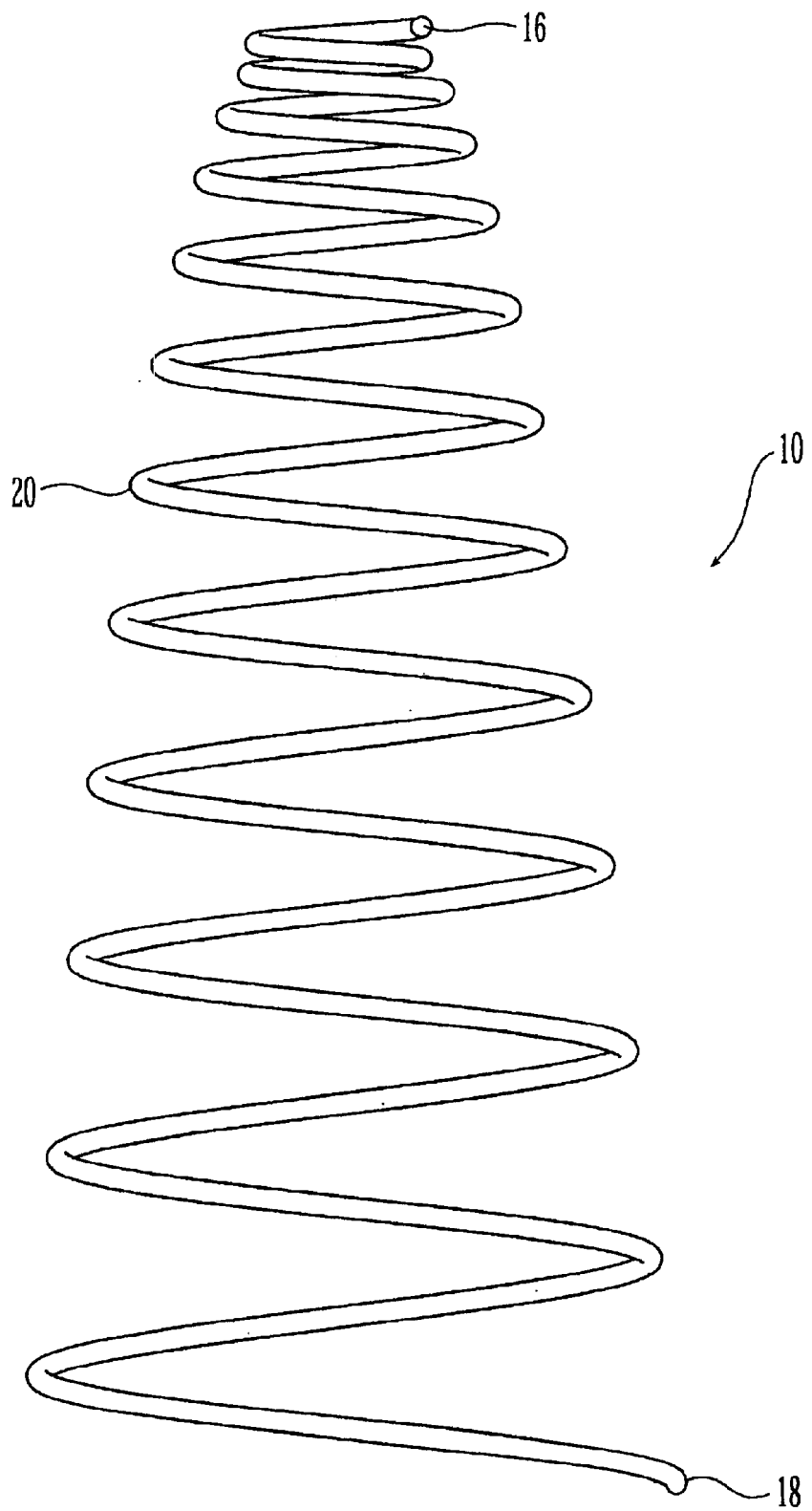
FIG. 5 is another side view of the conically coiled member of FIG. 2 rotated clockwise 90°.
Figure 6:
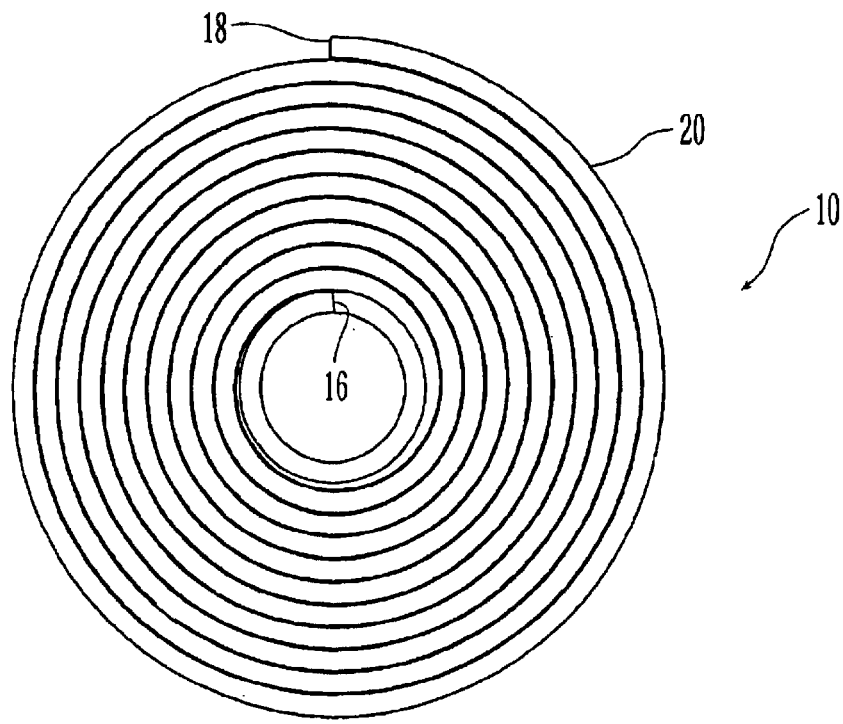
FIG. 6 is a top view of the conically coiled member of FIG. 2.
Figure 7:
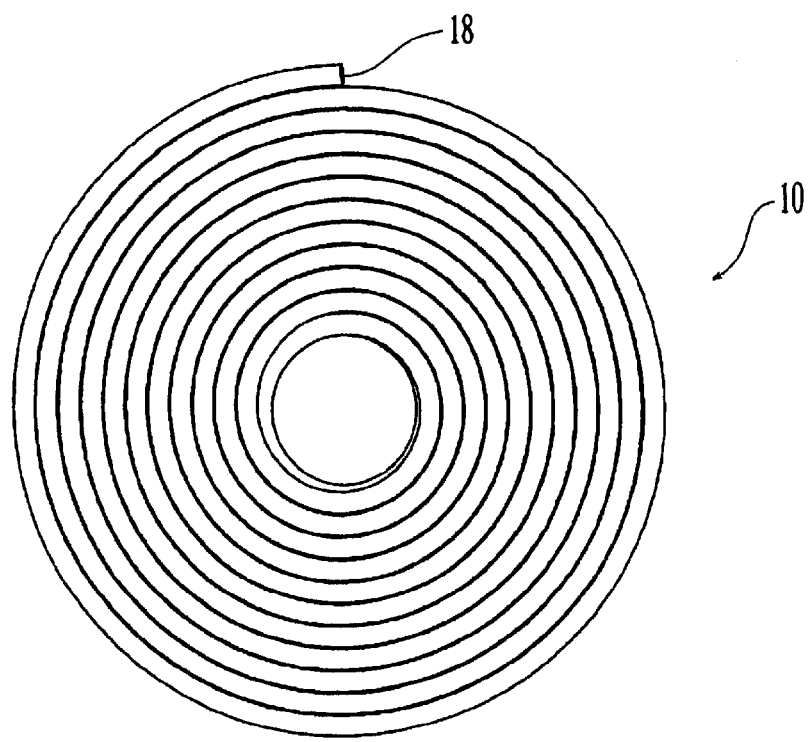
FIG. 7 is a bottom view of the conically coiled member of FIG. 2.

Referring to FIG. 1, there is shown a device or coil 10 that is formed in a conical spring configuration with a top end portion 12 and a bottom end portion 14. The coil 10 has a generally helical or spiral form. The top end 16 and bottom end 18 are joined by a series of loops 20. The loops 20 are coaxially disposed about a central longitudinal axis extending from the bottom end portion 14 to the top end portion 12. Coil 10 defines an inner area 13 and an outer area 15, the coil also having an inner surface 17 and outer surface 19 along each loop. In the embodiment illustrated in FIG. 1, the loops 20 decrease in diameter as they progress from the bottom end 18 to the top end 16. The coil in this embodiment is substantially conical, because it may not assume a perfectly conical configuration. Various side views of coil 10 are shown in FIGS. 2–5. For example, the coil 10 in FIG. 3 is rotated from the position shown in FIG. 2 clockwise 180° about the longitudinal axis extending from the bottom end portion 14 to the top end portion 12. FIG. 4 results from a counterclockwise rotation of 90°, while FIG. 5 results from a clockwise rotation of 90°. FIGS. 6 and 7 show the coil 10 from the top and bottom, respectively.

Figure 10:
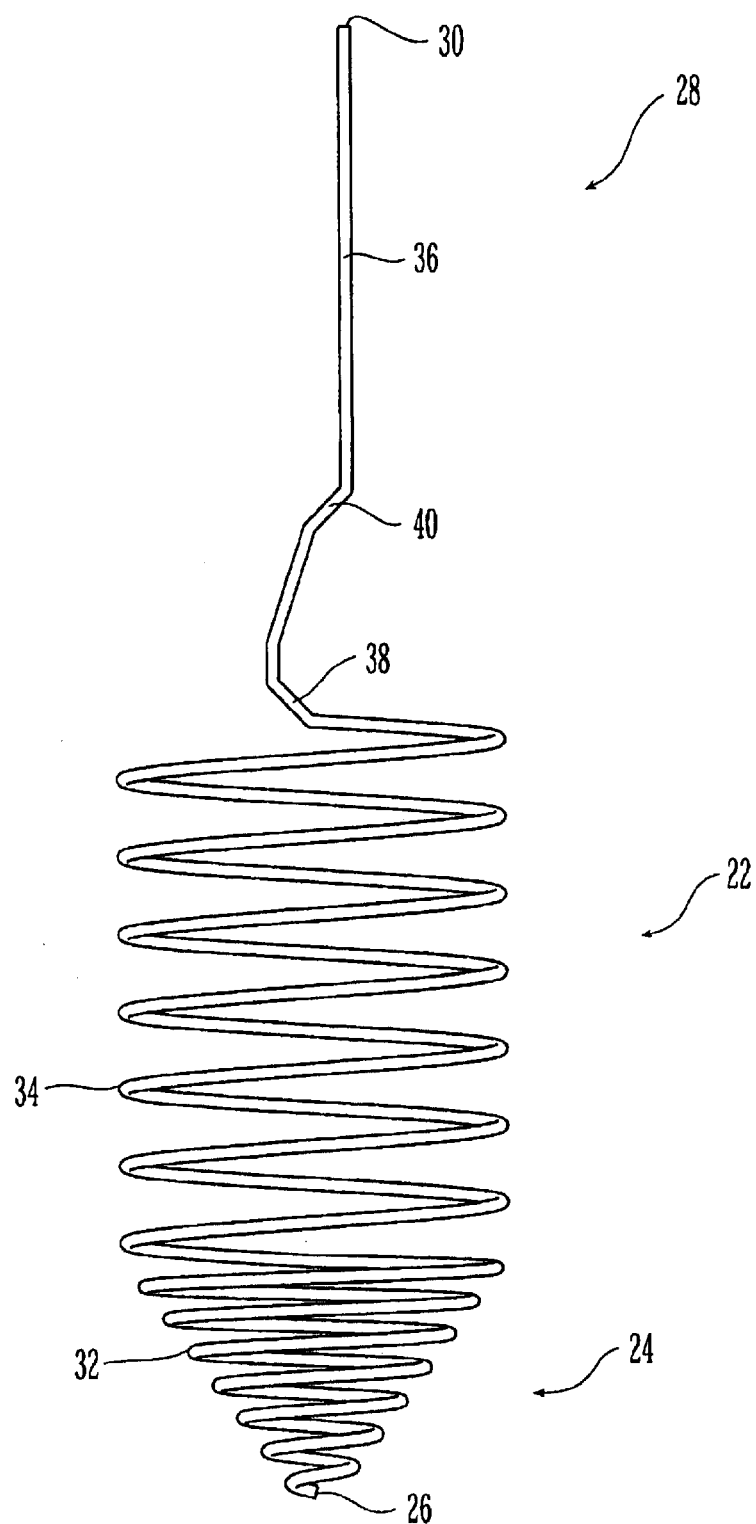
FIG. 10 is another side view of the coiled member of FIG. 9 rotated counterclockwise 180°.
Figure 11:
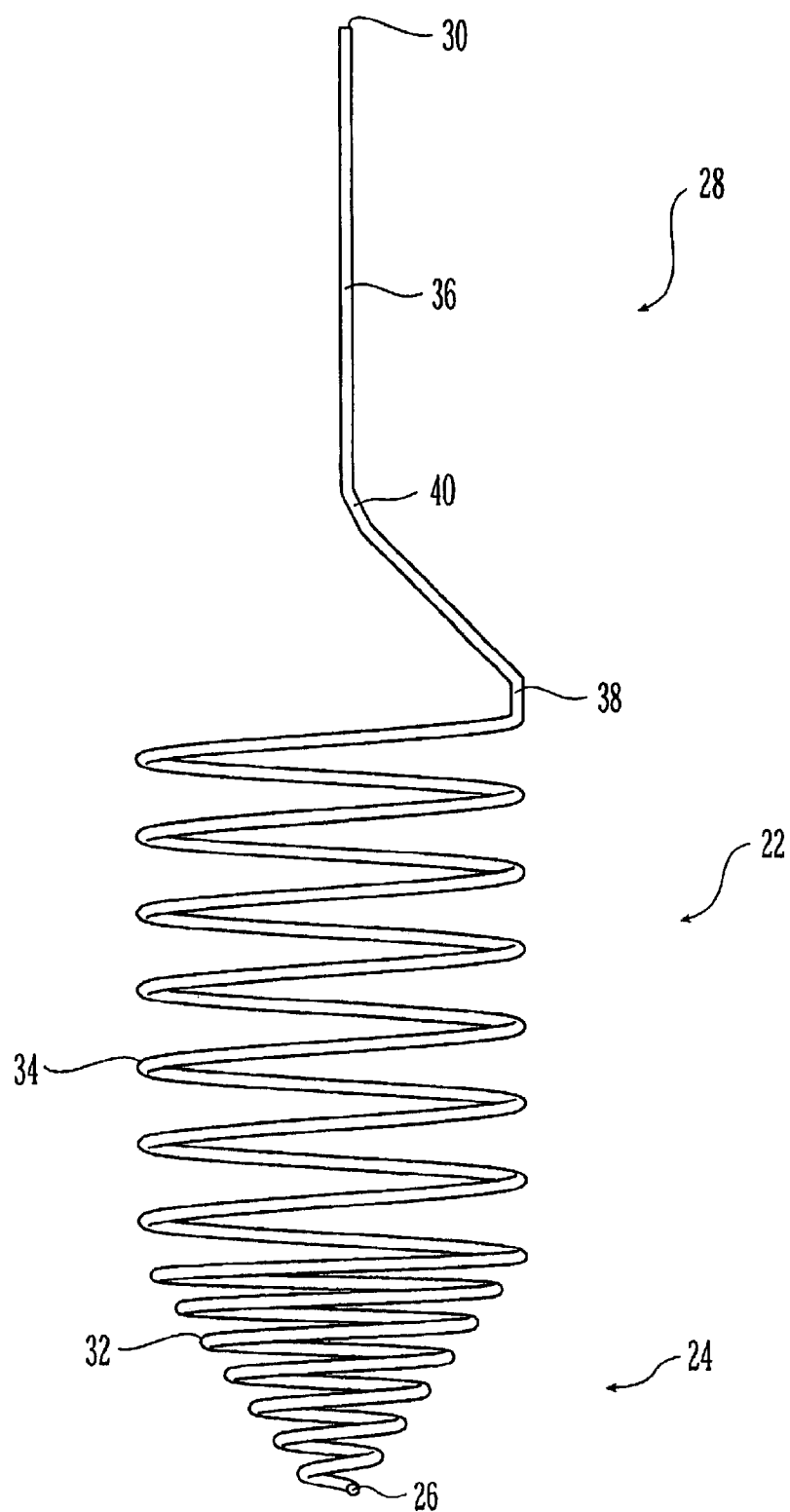
FIG. 11 is another side view of the coiled member of FIG. 9 rotated counterclockwise 90°.
Figure 12:
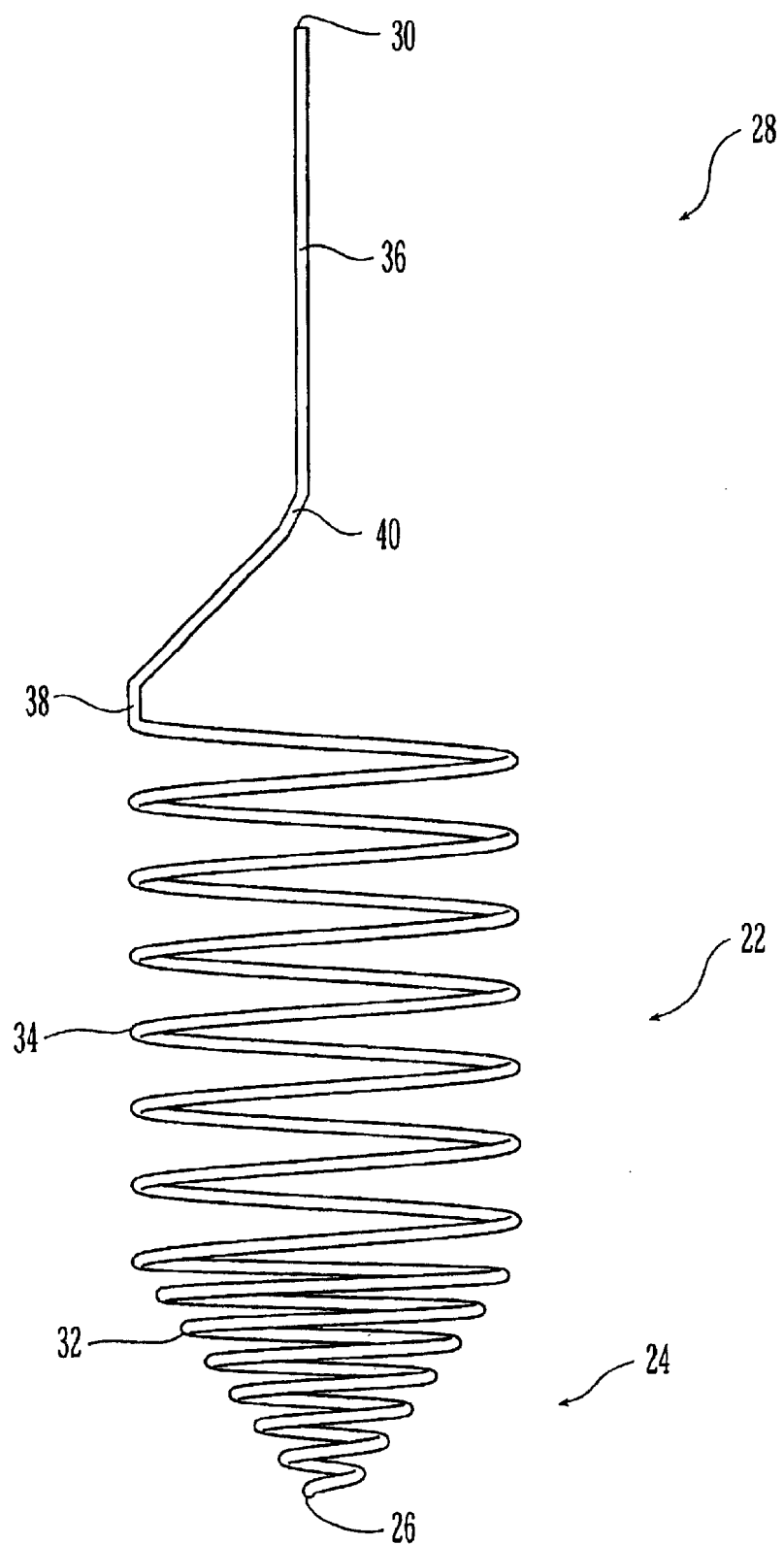
FIG. 12 is another side view of the coiled member of FIG. 9 rotated clockwise 90°.
Figure 13:
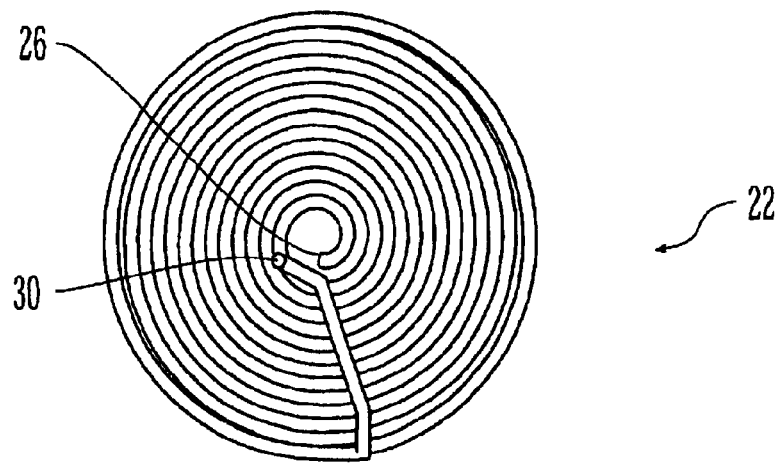
FIG. 13 is a bottom view of the coiled member of FIG. 9.
Figure 14:
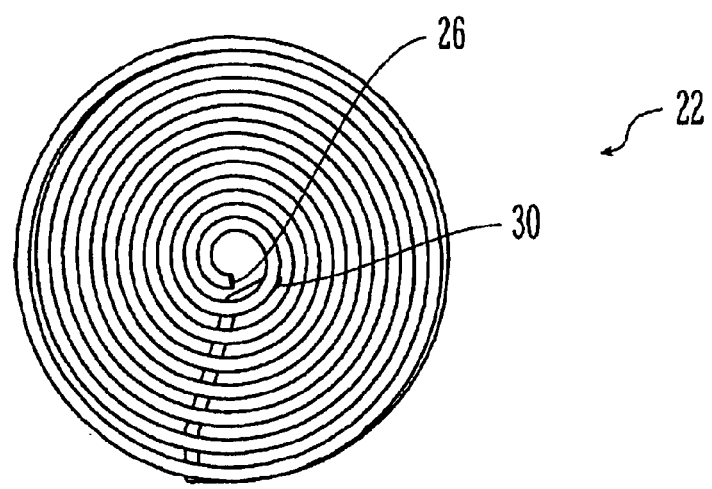
FIG. 14 is a top view of the coiled member of FIG. 9.

An alternative embodiment of the device 22 according to the present invention is shown in FIGS. 8–14. Device 22 includes an upper portion 24 having a top end 26 and a bottom portion 28 having a bottom end 30. Upper portion 24 has a substantially conical coiled section 32 followed by a substantially cylindrical section 34 and thereafter a generally linear section 36 that includes two crooked sections 38 and 40. The substantially conical and substantially cylindrical sections may not be precisely conical or cylindrical, respectively. As shown, the device 22 extends continuously from top end 26 to bottom end 30. Device 22 defines an inner area 33 and an outer area 35, the device also having an inner surface 37 and outer surface 39 along each loop. Various side views of device 22 are shown in FIGS. 9–13. For example, the device 22 in FIG. 10 is rotated from the position shown in FIG. 9 counterclockwise 180° about the longitudinal axis extending from the bottom portion 28 to the upper portion 24. FIG. 11 results from a counterclockwise rotation of 90°, while FIG. 12 results from a clockwise rotation of 90°. FIGS. 13 and 14 show the device 22 from the bottom and top, respectively.

In another alternate embodiment, not shown in the figures, the device 22 is substantially barrel shaped, or is provided with a substantially barrel shaped portion.

Figure 15K:
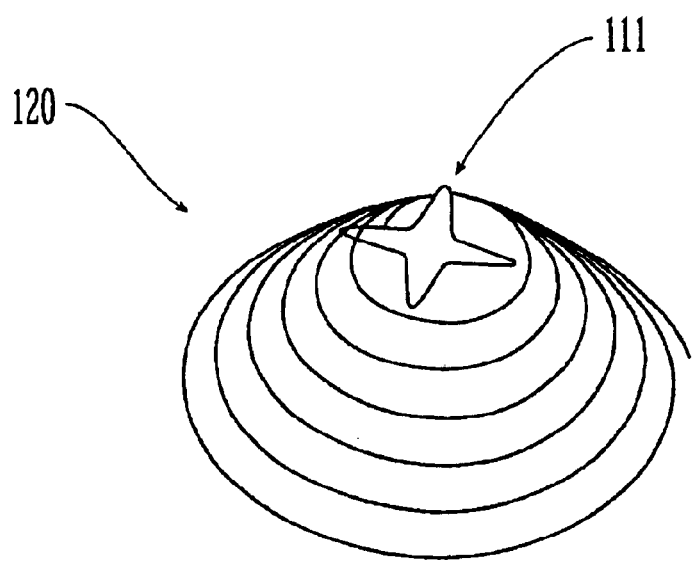
FIG. 15 is a collection of top views of various embodiments of coiled members according to the present invention, including (a)–(b) coils with loops that are not all coaxial about a central axis, (c) a coil with a lower, crooked anchor or clip section, (d)–(e) coils having lower anchors or clips with complex curvature, (f)–(k) coils having lower anchors or clips in fan or star-like configurations.

Various other configurations of coils according to the present invention are shown in FIG. 15. FIGS. 15(a)–(b) show coils 100 and 102, respectively, having loops that are not all coaxial about a central axis. FIG. 15(c) shows a coil 104 having a lower, crooked anchor section. FIGS. 15(d)–(e) show coils 106 and 108, respectively, having lower anchors with complex curvature. Also, FIGS. 15(f)–(k) show coils 110, 112, 114, 116, 118, and 120, respectively, having lower anchors or clips in fan or star-like configurations. Preferably, each clip has at least two prongs for contacting the tissue at the anatomical defect. The prongs may be curved prongs 109 and/or sharp prongs 111. Advantageously, the use of prong configurations permits multiple anchor points to tissue adjacent the anatomical defect, and thus also provides additional securing of the device to the defect region.

The pitch of a coil, defined as the center-to-center distance between adjacent loops 20, may be constant or variable along the central longitudinal axis. The free length of the coil, defined as the overall length of the coil measured along the central longitudinal axis extending from the bottom end 18 to the top end 16, is chosen based on the geometry of the physiological defect in question. Additionally, the coils may be right-handed or left-handed spirals. Furthermore, the decrease in diameter of the loops may be constant or variable.

In the preferred embodiment, the coil is not close-wound with adjacent loops 20 contacting each other. Instead, the loops 20 forming the ends 18 and 16 do not contact adjacent loops. Alternatively, the coil may be provided in close-wound form.

Figure 16:
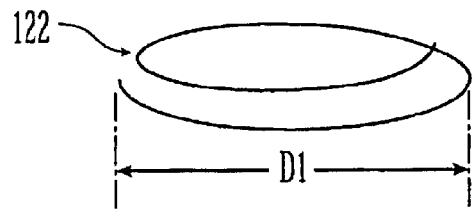
FIG. 16 is a perspective view of an alternate embodiment of a coiled member according to the present invention and having 1.5 loops.
Figure 17:
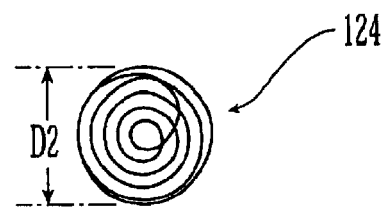
FIG. 17 is a top view of another alternate embodiment of a coiled member according to the present invention.
Figure 18:
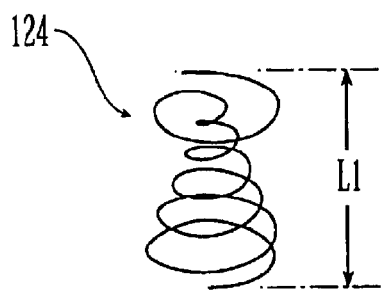
FIG. 18 is a perspective view of the coiled member of FIG. 17.

Another configuration of a coil according to the present invention is shown in FIG. 16. This coil 122 has only 1.5 loops. In a preferred embodiment, coil 122 has a maximum diameter of $D_1$ of 10 mm, and the total length of material used to form the coil is 44 mm. The radius of the full loop is different from the radius of the half loop. FIGS. 17–18 show yet another configuration of a coil according to the present invention. In a preferred embodiment, coil 124 has a maximum diameter of $D_2$ of 4.00 mm, and a maximum coiled length $L_1$ of 4.77 mm. In addition, the total length of material used to form coil 124 is 56 mm. Notably, the coil has a conical section with the smallest loop of the conical section also followed by a loop of larger diameter.

Figure 19:
FIG. 19 is a side view of another alternate embodiment of a coiled member according to the present invention.
Figure 20A:
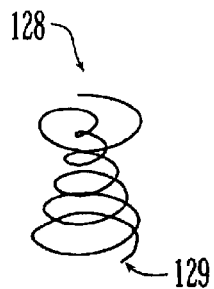
FIG. 20 is another embodiment of a coiled member according to the present invention, rotated in various orientations.
Figure 20B:
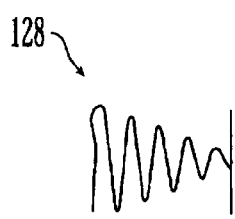
Figure 20C:
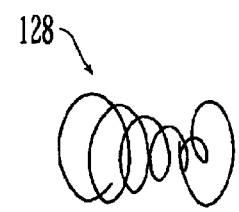
Figure 20D:
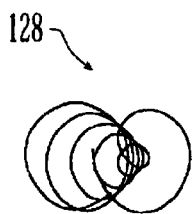
Figure 20E:
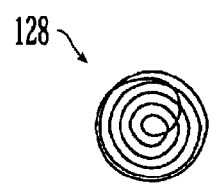
Figure 21A:
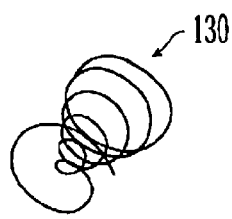
FIG. 21 is another alternate embodiment of a coiled member according to the present invention, rotated in various orientations.
Figure 21B:
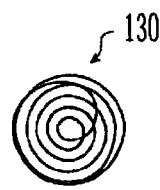
Figure 21C:
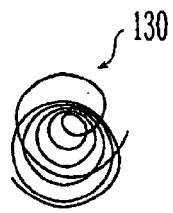
Figure 21D:
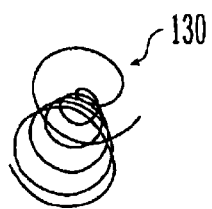
Figure 21E:
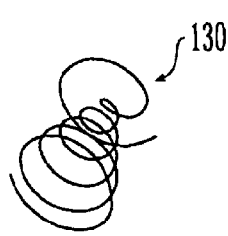
Figure 21F:
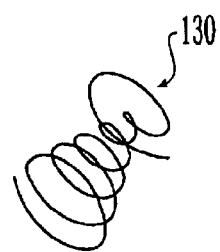

In another alternate embodiment shown in FIG. 19, a coil 126 has a generally conical profile, however the first and last loops each have a greater overall diameter than any of the intermediate loops.

FIGS. 20 and 21 show two additional coils 128 and 130, respectively, according to the present development, each rotated in several orientations. Each coil includes an anchor portion that spirals away from the coil. An anchor portion 129 is clearly shown, for example, at the bottom of FIG. 20(a). However, either end of the coil may serve this function.

FIGS. 22(a)–(d) show another coil according to the present development. Coil 132 has a first end 134 and second end 136. Although coil 134 is generally conical in overall shape, several loops are formed toward first end 134 such that an inner set of loops 138 and an outer set of loops 140 are formed. The inner set of loops 138 at first end 134 have a smaller diameter than the inner set of loops 138 at second end 136.

Figure 22A:
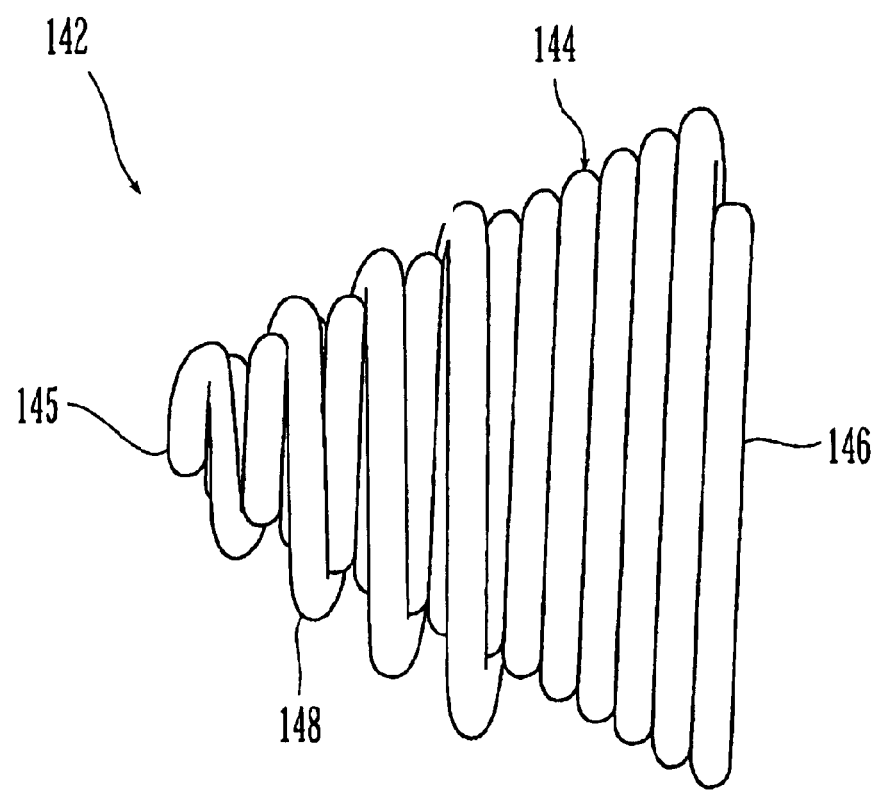
FIG. 22A is another embodiment of a coiled member according to the present invention, shown in side view.

In a variant of the coil shown in FIGS. 22(a)–(d), a coil 142 is shown in FIG. 22A with an inner set of loops 144 that form a cone from a first region 145 to a second region 146. An outer set of loops 148 also are provided, and extend from the narrow, first region 145. The inner set of loops 144 proximate first region 145 have a smaller diameter than the inner set of loops 144 at second region 146. In addition, in the embodiment as shown in FIG. 22A, the diameters of the outer set of loops 148 increase from the first region 145 toward the second region 146. When the coil is disposed in an anatomical defect region such as a hole, the outer set of loops may be disposed adjacent the ends of the hole and/or within the hole at a position along the hole length.

All embodiments of the coils may be adapted to include a clip on at least one of the coil ends. The clip enhances attachment of the coil to its surroundings. The clip may be a prong-like extension from the coil that has at least one generally straight section. Furthermore, the clip may be oriented transverse to the central longitudinal axis of the coil, or it may extend parallel to the axis. The choice of clip orientation may be partially determined by the type of anatomical defect to be filled. Alternatively, the clip may be in the form of a lower anchor with an arcuate configuration, or a complex structure such as a star-like configuration.

The closure device is a coil made of a shape memory alloy. Such a material may be deformed at a temperature below a transition temperature region that defines a region of phase change, and upon heating above the transition temperature region assumes an original shape. The coil is preferably made of an alloy having shape-memory properties, including, but not limited to, the following alloys: Ni—Ti, Cu—Al—Ni, Cu—Zn, Cu—Zn—Al, Cu—Zn—Si, Cu—Sn, Cu—Zn—Sn, Ag—Cd, Au—Cd, Fe—Pt, Fe—Mn—Si, In—Ti, Ni—Al, and Mn—Cu. The coil is most preferably made of a nickel-titanium alloy. Such nickel-titanium alloys have gained acceptance in many medical applications, including stents used to reinforce vascular lumens.

NiTi alloys are particularly suitable for coils because of their shape memory and superelastic properties. These alloys have two temperature-dependent phases, the martensite or lower temperature phase, and the austenite or higher temperature phase. When the alloy is in the martensitic phase, it may be deformed due to its soft, ductile, and even rubber-like behavior. In the austenitic phase, the alloy is much stronger and rigid, although still reasonably ductile, and has a significantly higher Young's Modulus and yield strength. While the material transforms from one phase to the other, the transformation temperature range is dependent on whether the material is being heated or cooled. The martensite to austenite transformation occurs during heating, beginning at an austenite start temperature, $A_s$, and ending at an austenite finish temperature, $A_f$. Similarly, the austenite to martensite transformation occurs during cooling, beginning at a martensite start temperature, $M_s$, and ending at a martensite finish temperature, $M_f$. Notably, the transition temperatures differ depending on heating and cooling, behavior known as hysteresis.

Some alloys display a "one-way" shape memory effect; essentially, this is an ability of the material to have a stored, fixed configuration (sometimes referred to as a trained shape), that may be deformed to a different configuration at a temperature below the phase change region, and subsequently may be heated above the transition temperature region to reassume that original configuration. A select group of alloys also display a "two-way" shape memory effect, in which the material has a first, fixed configuration at low temperature, and a second, fixed configuration at temperatures above the phase change. Thus, in this case, the material may be trained to have two different shapes.

Superelasticity (sometimes referred to as pseudoelasticity) occurs over a temperature range generally beginning at $A_f$, and ending when the NiTi is further heated to a martensite deformation temperature, $M_d$, that marks the highest temperature at which a stress-induced martensite occurs. In some cases, superelasticity may be observed at temperatures extending below $A_f$. The superelasticity of the material in this temperature range permits the material to be deformed without plastic deformation, and thus permanent deformation is avoided.

In order to fix the shapes that the NiTi is to assume, a proper heat treatment must be applied. Depending on the application and the particular shape-memory or superelastic effect to be used, shapes may be fixed at each of the desired temperatures above or below the transitions.

The various transition temperatures and other materials properties of Ni—Ti may be tailored to the application in question. Due to the solubility of alloying elements in the nickel-titanium system, it is possible to deviate from a 50—50 ratio of nickel to titanium, by having either more nickel or titanium, or by adding alloying elements in relatively small quantities. Typical dopants include chromium, iron, and copper, although other elements may be selectively added to affect the properties. In addition, mechanical treatments, such as cold working, and heat treatments, such as annealing, may significantly change the various properties of the material.

Although the Ni-50% Ti shape memory alloy is generally referred to as nitinol, an abbreviation for Nickel Titanium Naval Ordnance Laboratory that recognizes the place of discovery, the term as used herein extends to nickel-titanium alloys that deviate from this ratio and that also may contain dopants.

Figure 8:
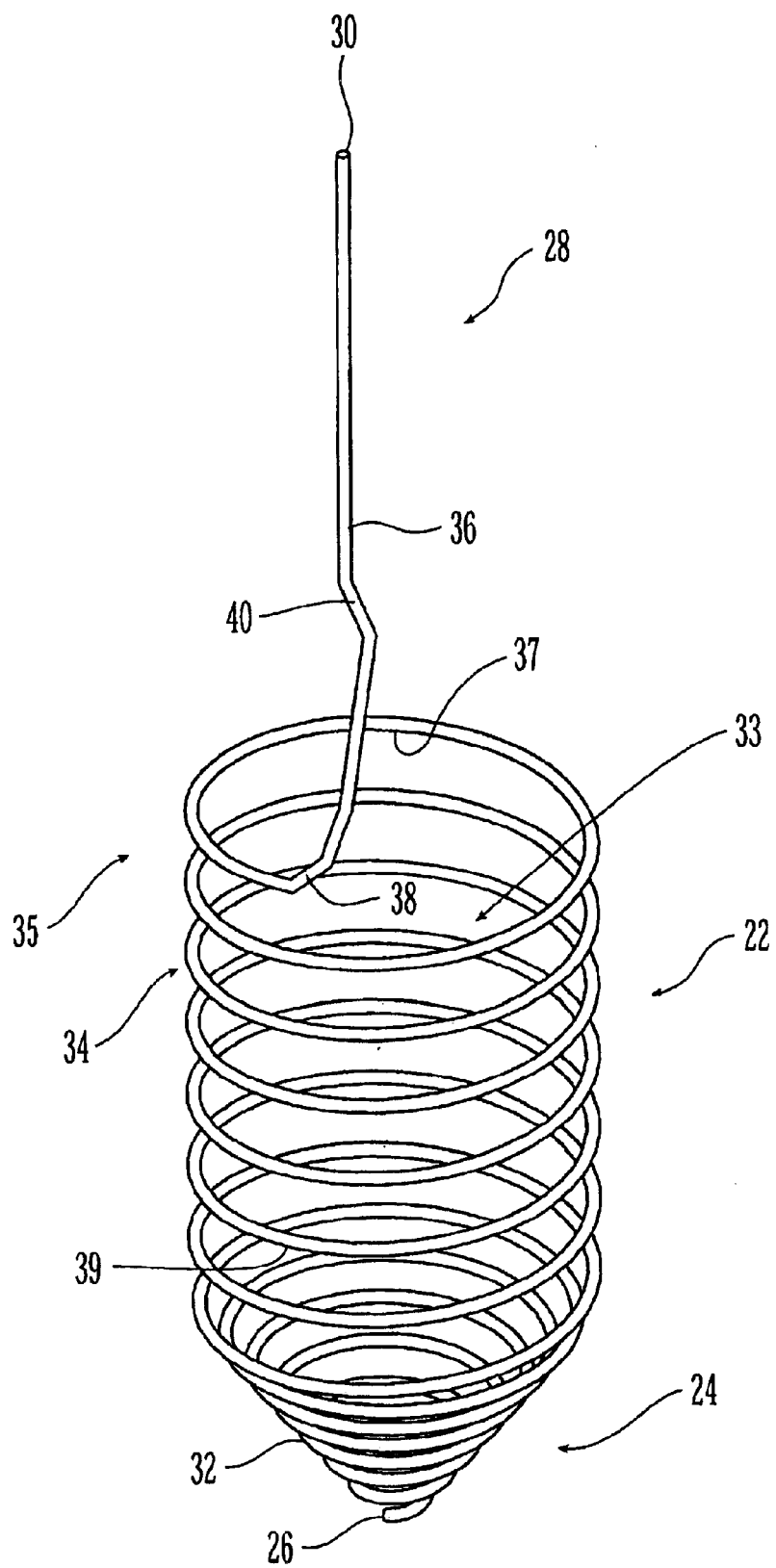
FIG. 8 is a perspective view of an alternate embodiment of a coiled member according to the present invention and having a configuration combining a conical portion, a cylindrical portion, and a generally linear portion.
Figure 9:
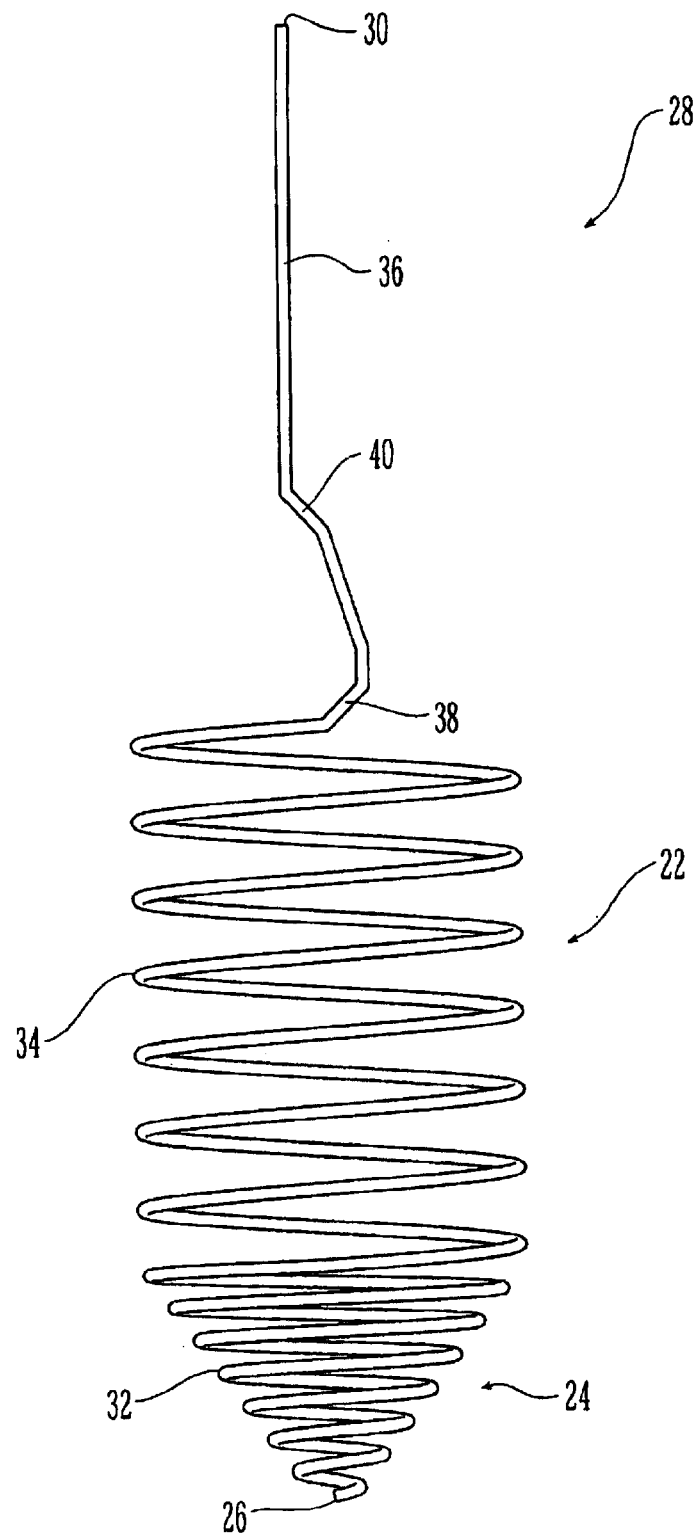
FIG. 9 is a side view of the coiled member of FIG. 8.

The present invention also relates to a method of manufacturing coils and delivery of those coils. A substantially straight piece of nitinol wire may be introduced into specific regions of the body, and thereafter assumes a pre-set geometry. The delivery may take place through a sheath that serves a similar purpose to that of a catheter, or the temporarily straightened coil may be delivered through specific catheters. The wire remains straight until it is exposed to the inside of the body. Upon reaching the end of the delivery system, and warming to a temperature between 30° C. and 40° C., the normal body temperature, the wire may assume a predetermined shape. In a preferred embodiment, the wire assumes a shape as shown in FIG. 1, 8 or 15. The choice of shape depends on the length of the wire introduced, as well as the anatomy where it is introduced. Various shapes are contemplated, including circular forms, rectangular forms, offset coiled forms having loops that are not coaxially disposed about a longitudinal axis, and concentric coiled forms, although the shape is not limited to these embodiments. In a preferred embodiment, the shape is helical, conical, or spiral. The wire may assume any open ended shapes as a final configuration, with the exception of a straight line.

As noted, the shape of the coil depends on the opening that needs to be filled with the coil. For example, in order to close the congenital malformation associated with a PDA, coils having shapes shown in FIGS. 1, 8 and 15 are appropriate. In a preferred embodiment, the maximum coil diameter is less than 1.5 cm. In another preferred embodiment, the sizes of the coil may be chosen as follows:

| maximum coil diameter (mm) | 4 | 5 | 6 | 7 | 8 | 9 |
|---|---|---|---|---|---|---|
| diameter of the last loop (mm) | 3 | 3.5 | 4 | 5 | 6 | 6 |
| side profile width (mm) | 3 | 4 | 4 | 4 | 4 | 4 |

For each coil, the last loop may be provided with a back clip which is not conical in shape, and this clip attaches the coil in the area of the malformation. Preferably, during delivery of the coil, as it exits the delivery catheter it warms and assumes its predetermined loop-like configuration. If a clip is included with the coil, preferably the clip is released last from the catheter.

The device may be delivered via a 5F (5 French) catheter that may be placed via a 6F sheath. In its substantially straight configuration, the device should snugly fit in the catheter for slidable delivery.

The introduction device may also include a small metallic tube that initially completely houses the straightened device. The tube may be temporarily attached to the proximal end of the catheter, and the device may subsequently be inserted into the catheter with the help of a guidewire. The guidewire preferably is substantially straight, has a diameter similar to that of the wire used to form the coil, and additionally has a generally stiff end and a soft end. Once the device has been completely placed in the catheter, the tube is discarded, and the guidewire is used to place the device at the distal tip of the catheter and effect delivery of the device to the desired anatomical location.

Generally, if the device must be retrieved due to improper positioning, the retrieval must occur prior to delivery of the final loop section of the coil. Otherwise, a more complex coil removal procedure may be necessary. In order to facilitate coil delivery, radiopaque markers may be provided on the device, and preferably are provided on a top side at proximal and/or distal ends. In an alternate embodiment, markers may be provided continuously or in spaced, regular intervals along the length of the device. The use of such markers allows device delivery to be precisely monitored. Thus, if a device is not delivered properly to the chosen anatomical location, the device may be withdrawn into the sheath for re-release or may be completely withdrawn from the body.

In order for coil retrieval to occur, the coil is gripped at one end using a jaw or other retention mechanism as typically used with biopsy-related devices. Alternatively, other coil delivery and retrieval procedures involving pressure may be used, i.e. air pressure and suction. Prior to completion of coil delivery, if for example improper coil alignment has resulted or an improper coil shape or size has been chosen, the retention mechanism may be used to withdraw the coil into the sheath.

Figure 23A:
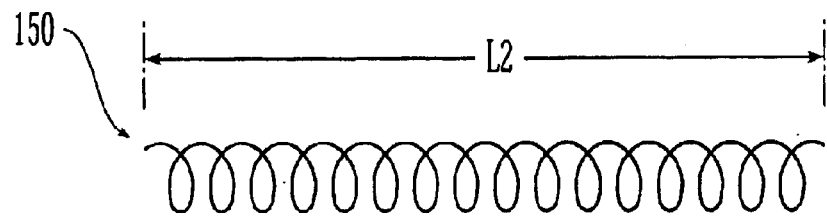
FIG. 23 is another embodiment of a coiled member according to the present invention, shown in (a) side view of the extended state, (b) side view of the final shape, and (c) perspective view of the final shape.
Figure 23B:
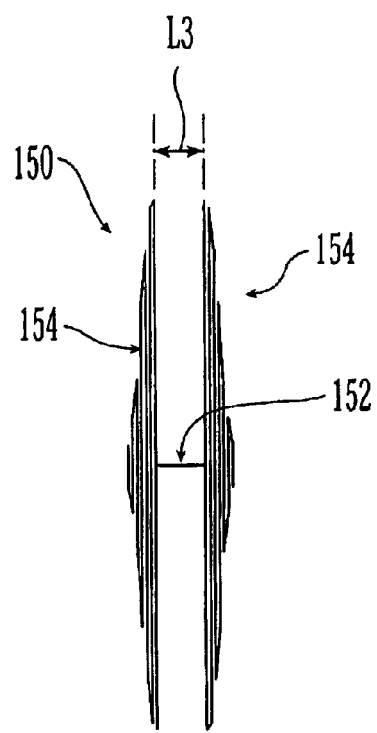
Figure 23C:
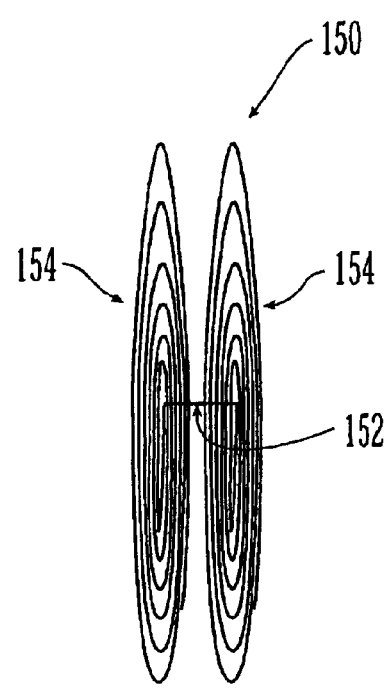

Alternatively, as shown in FIGS. 23–24, a coil 150 initially may be provided in an extended state such that its overall coiled length is $L_2$, and when delivered the coil assumes a final shape with an overall coiled length $L_3$. The final shape of coil 150 includes a transition section 152 between two spiral sections 154. Although the transition section 152 is generally straight in FIG. 23, transition section 152 may alternatively include loops forming a conical portion. Preferably, spiral sections 154 are formed such that the loops are generally coplanar. While coil movement may be constrained by a retention mechanism that, for example, grasps an end of a proximal portion of the coil, delivery of a coil such as coil 150 may be achieved using a movable sheath 156 and associated catheter.

Figure 24A:
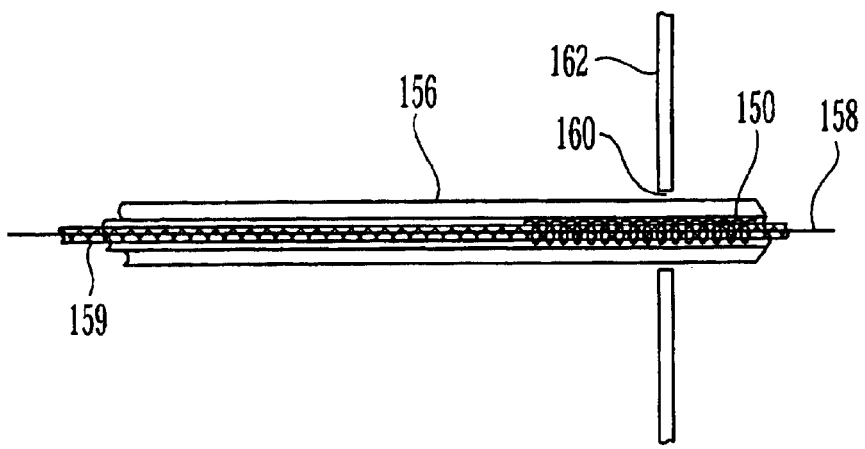
FIG. 24 is another embodiment according to the present invention, showing a sheath-based coil delivery system with partial side views of (a) the sheath and coil extended through an anatomical defect in tissue, (b) the sheath partially withdrawn and a portion of the coil exposed, and (c) the sheath completely withdrawn with the coil fully exposed.

A catheter may be used to deliver a coil 150 to an anatomical region. As shown in FIG. 24(a), a central shaft 158 is inserted through a hole 160 or other anatomical defect to be filled in tissue 162, which is depicted in partial side view. Such a hole 160, for example, may exist in a patient's heart in the septum. Central shaft 158 serves as a guidewire for the delivery of the coil. Preferably, central shaft 158 is surrounded by an inner sheath 159 formed of a braided metal wire having a layer of Teflon® (tetrafluoroethylene) on its inner surface for contacting central shaft 158 and a layer of Pebax® (polyether-block co-polyamide polymer) on its outer surface for contacting coil 150. With central shaft 158 in place, an outer movable sheath 156 is extended through hole 160 using central shaft 158 as a guide. Preferably, outer movable sheath 156 is formed from polyethylene terephthalate (PET) or nylon. Coil 150 is disposed between inner sheath 159 and outer movable sheath 156. Coil 159 is wound about inner sheath 159, and restrained from expanding in the radial direction by outer movable sheath 156.

Figure 24B:
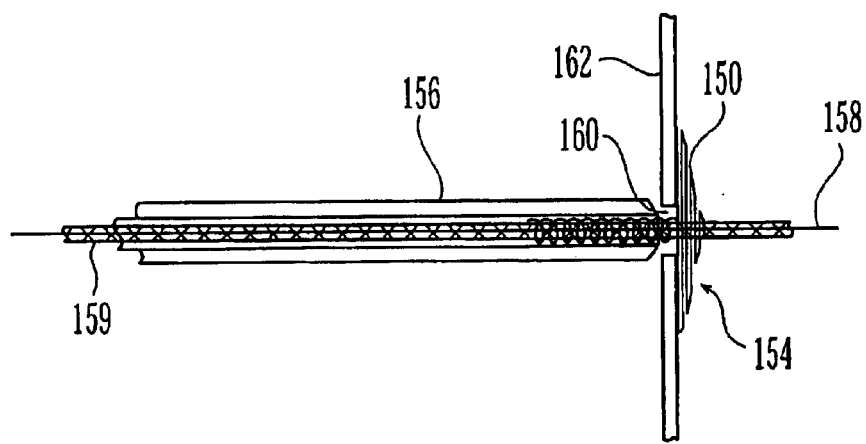
Figure 24C:
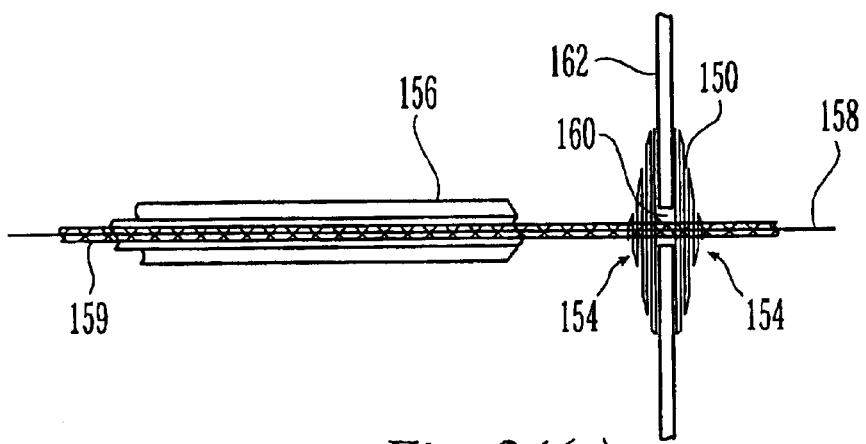

When outer movable sheath 156 is partially withdrawn, as shown in FIG. 24(b), a first, distal portion of coil 150 is exposed, warming to body temperature and thus assuming a preformed configuration. A first spiral section 154 forms on the far side of hole 160. Outer movable sheath 156 then may be further withdrawn, as shown in FIG. 24(c), exposing a transition portion of coil 150 and finally a proximal portion of coil 150 to the body, and thereby permitting coil 150 to assume the complete preformed configuration with a second spiral section 154 formed on the other, near side of hole 160. Coil 150 thus is held in place by the pressure applied by spiral sections 154 against tissue 162. A clip (not shown) also may be provided on one or both of spiral sections 154. A final coil release mechanism, such as a spring-release mechanism, may be used to separate coil 150 from the retention mechanism, and central shaft 158, inner sheath 159, and outer movable sheath 156 may be completely withdrawn from the body. A free end of coil 150 may be held by a biopsy forcep during the coil insertion procedure, to aid in the positioning and initial withdrawal of the sheath so that a spiral section 154 can be formed. In addition, the free ends of the coil may be capped or otherwise formed in the shape of beads. Such beads provide regions of increased thickness, and thus are detectable by x-ray equipment to aid in verification of coil positioning. The beads may also provide suitable structure for gripping by forceps. The sheath delivery method is particularly appropriate for the placement of coils having an overall length greater than twenty percent the length of the delivery catheter.

Several factors must be considered when choosing the size and shape of a coil to be used in a particular defect region. The desired helical diameter of the coil, a measure of the final diameter of the coil after expansion to its circular shape and implantation, must be considered in light of the geometry of the defect. In addition, the length of the coil and the number of coil loops must be considered. Furthermore, coils may be designed with tightly packed windings, windings having only a short distance between each loop, or loosely packed windings having greater separation between neighboring loops. The length of the coil places an additional constraint on the number of loops that may be provided. Coils may be packaged and provided to the medical community based on any of the aforementioned factors, or a combination thereof.

In a preferred embodiment, the coils are provided based on the substantially straightened length of the wire and/or the number of coil loops. Alternatively, the coils may be provided for selection based on coil length and/or helical diameter. In a simple case, if all loops had the same diameter, for example, the circumference of a representative loop could be determined by multiplying the helical diameter by $\pi$. The number of loops could thus be determined by a supplier or medical practitioner by dividing the substantially straightened length by the circumference of the representative loop. In designs having variable loop diameters, the circumferences of the individual loops must be known in order to determine the number of loops for a given length of wire.

In general, the coil size should be chosen to have a helical diameter approximately 20% to 30% larger than the narrowest size of the abnormality to be occluded. Otherwise, distal migration may occur if the coil is too small, and coils that are too large may be unable to fully assume their intended final geometry. Coils which assume the same size as the area to be occluded may still permit blood flow, and thus will fail to adequately fill the defect. The coil caliber is determined by catheter size used to cannulate the vessel.

In general, the helical diameter of the coil should be 2 to 3 times the size of the narrowest point of the duct to be occluded. This is especially appropriate for duct sizes less than about 2.5 mm. However, multiple coils may be required to achieve complete occlusion of some ducts. In particular, ducts greater than about 4 mm may require between 3 to 6 coils to effectuate complete occlusion. This is important, for example, in the treatments of PDAs having defect sizes as large as 7 mm.

The coil may be made thrombogenic by attaching or weaving fibers along the length of the coil. In a preferred embodiment, Dacron® (polyester) strands are used.

The wire used to form the coils preferably has an outer diameter of 0.018", 0.025", 0.035", or 0.038", and may be pre-loaded into a stainless steel or plastic tube for simple and direct insertion into the catheter or other delivery device. Several wires may be braided together in order to produce a wire with a desired outer diameter; for example, several wires each having outer diameters of approximately 0.010" may be used to create a wire having an overall outer diameter close to 0.038". Furthermore, a single wire may be encapsulated in a multi-strand braid.

The catheter chosen should be of soft material so that it may assume the shape of a tortuous vessel. Preferably, it should be free of any side holes, and the internal diameter should be chosen to closely mimic the internal diameter of the coil. Using a catheter of larger bore than the straightened length of the wire may cause the coil to curl within the passageway. The use of shape-memory wire allows the wire to have greater resiliency in bending, and thus permanent, plastic deformations may still be avoided even if difficulties are encountered during wire delivery.

The importance of duct characterization cannot be over-emphasized. The safest ducts to occlude are those which funnel into small areas. All ducts, however, do not fit this profile. Some ducts, for example, have a very short area of narrowing, followed by a widened portion. Additionally, some ducts have relatively long lengths with a relatively narrow diameter, followed by lengths with wider diameter. Proper choice of coil and delivery technique allows these ducts to be occluded as well.

Vessels with a serpentine configuration may complicate the coil delivery procedure. A vessel that is too tortuous may be inaccessible if standard catheters are employed. However, smaller catheters such as Tracker catheters may permit the vessel to be more easily negotiated, such as in cases of coronary AV fistulas. The advantage of such Tracker catheters is their ability to be tracked to the distal end of the fistula. The catheter is passed through larger guiding catheters which may be used to cannulate the feeding vessel such as the right or left coronary artery at its origin. Such a Tracker catheter may accommodate 0.018" "micro-coils".

Alternatively, in order to accommodate large coils such as 0.038" coils, 4F catheters such as those made by Microvena may be employed. For defects requiring such large coils, delivery may be made either from the arterial or venous end. Damage to the artery may be minimized if the femoral artery route is approached.

In patients requiring multiple coils, delivery may occur sequentially by accessing the duct in an alternating sequence from the arterial or venous route, or by simultaneous delivery from each route. In the latter case, the duct may be accessed by two or three catheters usually from the venous end. At least two coils may be released simultaneously in the aortic ampulla, with the pulmonary ends of the coils released sequentially. A third coil may be subsequently released through a third catheter placed at the duct. The advantage of the simultaneous technique is the ability to occlude very large ducts with individual coil sizes that are less than two or three times the size of the duct. Both techniques may also be used in combination.

An example of multiple coil deployment is illustrative. In order to occlude a 5.7 mm duct, two 8 mm coils along with one 5 mm coil were deployed by the simultaneous technique as previously described. Subsequent to this deployment, three additional 5 mm coils were deployed using the sequential technique, in order to achieve complete occlusion. This combined use of deployment techniques was essential to the success of the procedure, since use of only the sequential approach in this case would have theoretically necessitated a coil approximately 12 to 16 mm in size. Such an extreme size may be particularly troublesome in young children, and may result in unacceptable blockage of the pulmonary artery or protrusion beyond the aortic ampulla. In addition, such a large coil might result in a high incidence of embolization of the first one or two coils.

In order to decrease the incidence of coil embolization, a controlled release coil is useful. Such a spring coil design, reminiscent of the Gianturco coil, may be provided with a central passageway through which a delivery mandril is passed. Interlocking screws between the spring coil and the delivery wire assist in securing the coil until it has been delivered to a proper position in the duct. The coil may then be released by unscrewing the locking device. The use of this controlled release technique has been attributed to a decrease from 9% to only 1.8% in the incidence of coil embolization.

In another preferred embodiment of the coil design, a plurality of active memory and passive memory elements are used. Advantageously, such a combination permits a desired coil stiffness and length to be achieved, and further facilitates the use of coils with extended ends or clips. In a preferred method of fabricating the coil, a coil wire is wound on top of a core wire using conventional winding techniques to create a multilayered wire. Preferably, a high precision winding device is used, such as the piezo-based winding system developed by Vandais Technologies Corporation of St. Paul, Minn. The coil wire is preferably rectangular or arcuate in cross-section, but other cross-sections such as a hexagonal shape or other polygonal shape may be used. The coil wire is also preferably substantially uniform in cross-section. However, a gradually tapered wire may also be used. Preferably, the dimensions of the layered coils are chosen such that comparatively thick sections formed from passive materials are avoided, due to expansion difficulties that may arise when the coils are warmed to their preset configuration. Subsequent to winding the coil wire/core wire combination, the multilayered wire is wound about a mandrel having a desired shape, preferably a shape permitting a final coil configured as shown in FIG. 1, 8 or 15. The coil may also be formed with or without clips for anchoring the device at or near the site of the anatomical defect. The entire assembly is next transported to a furnace, wherein the multilayered wire is heat treated to set the desired shape. The temperature and duration of any heat treatment is a function of the materials used to form the multilayered wire. Following heat treatment, the assembly is removed from the furnace and allowed to cool to room temperature. The coil may then be removed from the mandrel. Depending on the materials used for the core wire and coil wire, a coil having a combination of active and passive memory elements may be produced.

In some alternate embodiments, the heat treating of the wire formed from a shape memory material is performed prior to winding a non-shape memory wire about it.

For example, nitinol coil wire may be used to confer active memory to the device, due to its shape memory and/or superelastic properties. Stainless steel, carbon fiber, or Kevlar® (poly-paraphenylene terephthalamide) fiber core wire may be used to confer passive memory because they are materials that may be given heat-set memory, but do not possess shape memory properties. Other appropriate passive-memory materials include relatively soft metals such as platinum and gold, relatively hard metals such as titanium or Elgiloy® (Cobalt-Chromium-Nickel alloy), or non-metals such as polytetrafluoroethylene (PTFE) or Dacron® (polyester, synthetic or natural fiber). The multilayered wire advantageously allows the device to possess several distinct materials properties; a wire layer of carbon fiber may allow an extremely flexible device shape, while a wire layer of nitinol may provide necessary rigidity. This combination enhances the ability of the device to retain its shape regardless of the type of defect or forces encountered during deployment and usage. Furthermore, the carbon fiber or other passive material facilitates the navigation of the device through tortuous anatomical regions.

If carbon fiber is used as the core wire, then the coil wire cannot be wound directly on the core. In such a case, a suitable mandril is first used to wind the coil wire, which is next subjected to a heat treatment in a furnace. After removal from the furnace and cooling, the mandril is removed and the carbon fiber is placed on the inner surface of the coil wire.

Alternatively, the madril may be removed after winding the coil wire, so that the core wire may be placed on the inner surface of the coil wire. The multilayered wire may then again be placed on the mandril, and subjected to a heat treatment to set the desired shape.

In an alternate embodiment, the coil wire is bordered by a core wire on the inner surface of the device, and an additional overlayer wire on the outer surface of the device. In yet another embodiment, the coil wire is provided as a twisted pair with the second wire of the pair being formed of either an active memory material or a passive memory material.

In yet another alternate embodiment of a coil and method of fabricating a coil having a combination of active memory and passive memory elements, a core wire is wound on top of a coil wire. The coil wire may serve as either the active or passive memory element. Likewise, the core wire may serve as either the active or passive memory element.

Figure 25A:
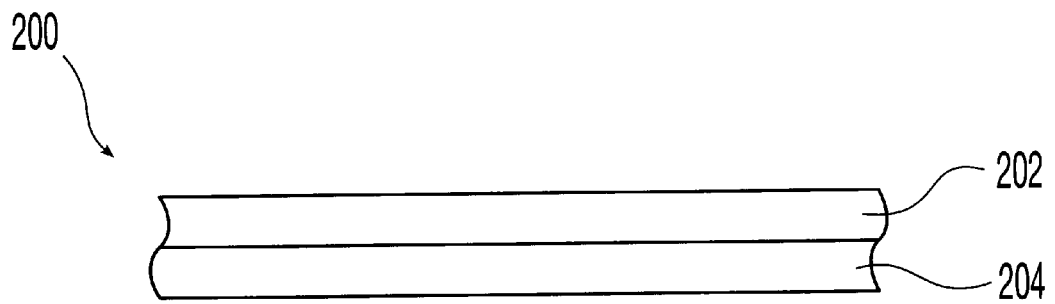
FIG. 25(a) is a side view of a member formed of two layers.

In addition, the core and coil wires may be disposed about each other in various configurations. The core wire, for example, may be disposed longitudinally about the coil wire (i.e., oriented in mirror-image fashion). For example, as shown in FIG. 25(a), a member 200 may be formed of layers 202, 204. Alternatively, the core wire may be wrapped about the coil wire in spiral fashion. If several core wires or several coil wires are to be used in combination, the wires may be disposed about each other using one or both of the longitudinal planking or radial wrapping orientations.

In a preferred embodiment, a capping process may also be undertaken to allow the ends of the core and the wire to be welded and capped in order to avoid any fraying.

Figure 25B:
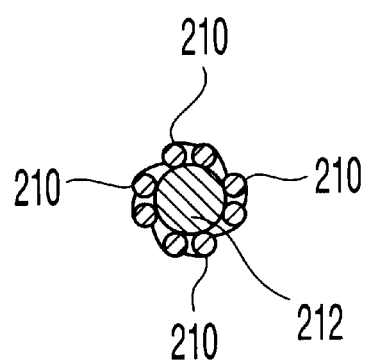
FIG. 25(b) is a cross-sectional view of a braid portion disposed around a central core.

In another preferred embodiment, a braid may also be wound on top of a central core. The braid may be wound to a desired pitch, with successive turns oriented extremely close together or at varying distances apart. For example, as shown in FIG. 25(b), braid portions 210 may be disposed around a central core 212. When braids are wound in spaced fashion, the mandril is left exposed at various intervals. After the madril is removed, a suitable intermediate material may be used in its place.

Various central core materials are contemplated, including plastic, metal, or even an encapsulated liquid or gel. In a preferred embodiment, an active memory/active memory combination is used, thus necessitating central cores and braids made of shape memory materials. In a most preferred embodiment, the central core and braid are both made of nitinol.

In an alternate embodiment, one of the central core and braid is an active memory element and the other is a passive memory element.

After the multilayered wire is wound on the core using a winding machine, the wound material may be released from the tension of the machine. If nitinol is used, the superelastic properties of the nitinol produce a tendency of the wound form to immediately lose its wound configuration. In order to retain the shape, an external mechanical or physical force may be applied, such as a plastic sleeve to constrain the material. If a plastic sleeve is used, it may be removed prior to heat treatment.

A multi-part mold may also be used. Due to the superelastic properties of nitinol wire, it may be necessary to further constrain the wire on the mandril during the manufacturing process. Thus, an inner mandril may be used for winding the wire to a desired shape. After winding, an outer mold may be used to completely surround the wire on the mandril to constrain its movement with respect to the mandril. The mandril and mold create a multi-part mold that may be transferred to a furnace for the heat treatment process. In a preferred heat treatment, the wire must be heated to a temperature of approximately 450–600° C. Depending on the material used to form the multi-part mold, the mold may need to be heated to a suitably higher temperature in order for the wire encased within the mold to reach its proper heat set temperature. Only a short heat treatment at the set temperature may be required, such as thirty minutes. After cooling, the device must be removed from the multi-part mold and carefully inspected for any surface or other defects.

In a preferred embodiment, the coil device is provided with at least one clip, located at the end of a loop. The clip allows the device to be anchored in the desired anatomical region of the body.

Due to the superelastic and shape memory properties of nitinol, various devices are contemplated. The superelastic properties allow the coils to have excellent flexibility, while the shape memory properties allow the coils to be delivered through conventional catheters that otherwise could not easily accommodate the diverse defect shapes.

While various descriptions of the present invention are described above, it should be understood that the various features may be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for occluding an anatomical defect, comprising a wire member formed of a shape memory alloy, the member having a free bottom end and a free top end, a first predetermined unexpanded shape, and a second predetermined expanded shape, wherein the unexpanded shape is substantially linear and the expanded shape is substantially conical, the expanded shape having a plurality of loops coaxially disposed about a longitudinal axis, the loops progressively decreasing in diameter from one end of the device to the other, wherein at least one of the ends of the member includes a clip having a non-overlapping planer fan-like configuration with at least two prongs for contacting areas adjacent the anatomical defect.

2. The device of claim 1, wherein the loops form a substantially conical coil having a constant pitch.

3. The device of claim 1, wherein the loops form a substantially conical coil having a variable pitch.

4. The device of claim 1, wherein the shape memory alloy is a nickel-titanium alloy.

5. The device of claim 1, wherein the member is substantially arcuate in cross-section.

6. The device of claim 1, wherein at least one of the prongs has a sharp portion for attaching to an area adjacent the defect.

7. The device of claim 6, wherein the diameter of the plurality of loops is smaller than about 1.5 cm.

8. The device of claim 7, wherein the shape memory alloy displays a one-way shape memory effect.

9. The device of claim 8, wherein the shape memory alloy displays a two-way shape memory effect.

10. The device of claim 8, wherein the shape memory alloy has an austenite finish temperature below body temperature, thereby permitting the device to have superelastic properties at body temperature.

11. The device of claim 8, wherein the shape memory alloy displays a superelastic effect at body temperature.

12. A device of claim 1, wherein the shape memory alloy member includes a plurality of layers.

13. The device of claim 12, wherein the plurality of layers includes at least one layer formed of a passive memory material.

14. The device of claim 12, wherein the plurality of layers includes at least two layers formed of active memory materials.

15. The device of claim 14, wherein at least one of the layers is a wire formed of a shape memory material, and at least one of the layers is a braid Conned of a shape memory material.

16. The device of claim 12, wherein the plurality of layers includes at least two layers braided together or one layer surrounded by a braid.

17. The device of claim 1 further comprising at least one crooked section, a substantially conical section, and a substantially cylindrical section disposed between the crooked section and the conical section.

18. A wireform for occluding an anatomical defect comprising a free bottom end, a free top end, a first predetermined unexpanded configuration, and a second predetermined expanded configuration, wherein the unexpanded configuration is substantially linear, the expanded configuration is substantially conical and includes a plurality of loops progressively decreasing in diameter between the ends of the wireform, the wireform comprises a shape memory material, and at least one of the ends includes a non-overlapping planer fan-like configuration having at least two prongs for contacting areas adjacent the anatomical defect.

19. The wireform of claim 18, wherein the shape memory material comprises a shape memory alloy.

20. A wireform for occluding an anatomical defect comprising:

a free bottom end, a free top end, a first predetermined unexpanded configuration, and a second predetermined expanded configuration;

wherein the wireform comprises a shape memory material;

the unexpanded configuration is substantially linear;

the expanded configuration includes at least one crooked section, a substantially conical section, and a substantially cylindrical section disposed between the crooked section and the conical section; and at least one of the ends includes a non-overlapping planer fan-like configuration having at least two prongs integrally formed therewith for contacting areas adjacent the anatomical defect.

21. The wireform according to claim 20, wherein the wireform is substantially arcuate in cross-section.

* * * * *

UNITED STATES PATENT AND TRADEMARK OFFICE
CERTIFICATE OF CORRECTION

PATENT NO. : 6,790,218 B2 Page 1 of 1
APPLICATION NO. : 09/739830
DATED : September 14, 2004
INVENTOR(S) : Swaminathan Jayaraman It is certified that error appears in the above-identified patent and that said Letters Patent is hereby corrected as shown below:

Column 17
Claim 15, line 32, change "Conned" to --formed--

Signed and Sealed this

Thirty-first Day of October, 2006

JON W. DUDAS
*Director of the United States Patent and Trademark Office*